(12) United States Patent
Brewer et al.

(10) Patent No.: US 8,215,306 B2
(45) Date of Patent: Jul. 10, 2012

(54) RESPIRATORY ACCESS PORT ASSEMBLY WITH PUSH BUTTON LOCK AND METHOD OF USE

(75) Inventors: John Brewer, Marietta, GA (US); Cassandra E. Morris, Roswell, GA (US); Joe Gordon, Mansfield, MA (US); Stephen Gianelis, Abington, MA (US); Dave Zitnick, Providence, RI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 651 days.

(21) Appl. No.: 12/395,664

(22) Filed: Feb. 28, 2009

(65) Prior Publication Data
US 2010/0147310 A1 Jun. 17, 2010

Related U.S. Application Data

(63) Continuation-in-part of application No. 12/333,916, filed on Dec. 12, 2008, now abandoned.

(51) Int. Cl.
*A61M 1/00* (2006.01)
*A61M 16/00* (2006.01)
(52) U.S. Cl. ............... 128/207.14; 604/319; 604/540; 128/207.15
(58) Field of Classification Search .......... 604/540, 604/319; 128/207.14, 207.15
See application file for complete search history.

(56) References Cited

U.S. PATENT DOCUMENTS

| | | | |
|---|---|---|---|
| 4,270,778 A | 6/1981 | Brownell | |
| 4,326,520 A | 4/1982 | Alley | |
| 4,569,344 A | 2/1986 | Palmer | |
| 4,641,646 A | 2/1987 | Schultz et al. | |
| 4,836,199 A | 6/1989 | Palmer | |
| 5,158,569 A | 10/1992 | Strickland et al. | |
| 5,207,641 A | 5/1993 | Allton | |
| 5,255,672 A | 10/1993 | Jinotti | |

(Continued)

FOREIGN PATENT DOCUMENTS
DE      29 39 794 A1     4/1981
(Continued)

*Primary Examiner* — Melanie Hand
(74) *Attorney, Agent, or Firm* — James B. Robinson; Sue C. Watson

(57) ABSTRACT

A respiratory access assembly inctudes a distal pJate having one port and cuff and an axially aligned proximal plate including a first port and first cuff and a second port and second cuff. The distal plate is configured to move relative to the proximal plate. The respiratory access assembly includes an actuator, which has a plurality of predetermined positions. When the actuator is positioned in a movement-enabling position, it permits movement of the plates while simultaneously blocking the first port of the proximal plate. When the actuator is positioned in a first or second locked (open) position, it locks the plates together and aligns the port of the distal plate with the respective first or second port of the proximal plate and un-blocks the first port of the proximal plale so that an object, such as a suction catheter, may be positioned through the aligned ports. When the actuator is positioned in the third locked (closed) position, it locks the plates together such that the port of the distal plate is positioned between the first port and the second port or the proximal plate and all ports are out of alignment with each other, such that all ports are blocked by a portion of one plate so that no object is moveable through any of the ports. A method of using a respiratory access assembly is provided.

13 Claims, 20 Drawing Sheets

U.S. PATENT DOCUMENTS

| | | | |
|---|---|---|---|
| 5,309,902 A | 5/1994 | Kee et al. | |
| 5,333,606 A | 8/1994 | Schneider et al. | |
| 5,333,607 A | 8/1994 | Kee et al. | |
| 5,335,655 A | 8/1994 | Kee | |
| 5,337,780 A | 8/1994 | Kee | |
| 5,343,857 A | 9/1994 | Schneider et al. | |
| 5,354,267 A | 10/1994 | Niermann et al. | |
| 5,357,946 A | 10/1994 | Kee et al. | |
| 5,377,672 A | 1/1995 | Kee | |
| 5,445,141 A | 8/1995 | Kee et al. | |
| 5,540,668 A | 7/1996 | Wilson, Jr. et al. | |
| 5,628,306 A | 5/1997 | Kee | |
| 5,694,922 A | 12/1997 | Palmer | |
| 5,730,123 A | 3/1998 | Lorenzen et al. | |
| 5,735,271 A | 4/1998 | Lorenzen et al. | |
| 5,738,091 A | 4/1998 | Kee et al. | |
| 5,746,199 A | 5/1998 | Bayron et al. | |
| 5,882,348 A | 3/1999 | Winterton et al. | |
| 5,916,201 A | 6/1999 | Wilson, Jr. et al. | |
| 6,012,451 A | 1/2000 | Palmer | |
| 6,070,582 A | 6/2000 | Kee | |
| D448,842 S | 10/2001 | Madsen et al. | |
| D448,843 S | 10/2001 | Madsen et al. | |
| D449,106 S | 10/2001 | Madsen et al. | |
| D449,107 S | 10/2001 | Madsen et al. | |
| 6,494,203 B1 | 12/2002 | Palmer | |
| 6,609,520 B1 | 8/2003 | Carlsen et al. | |
| 6,612,304 B1 | 9/2003 | Cise et al. | |
| 6,615,835 B1 | 9/2003 | Cise et al. | |
| 6,629,530 B2 | 10/2003 | Cise | |
| 6,698,424 B2 | 3/2004 | Madsen et al. | |
| 6,729,326 B1 | 5/2004 | Winterton et al. | |
| 6,811,142 B2 | 11/2004 | Svendsen | |
| 6,923,184 B1 | 8/2005 | Russo | |
| 6,978,783 B2 | 12/2005 | Svendsen | |
| 7,021,313 B1 | 4/2006 | Crump et al. | |
| 7,188,623 B2 | 3/2007 | Anderson et al. | |
| 7,191,782 B2 | 3/2007 | Madsen | |
| 7,263,997 B2 | 9/2007 | Madsen et al. | |
| 7,353,822 B2 * | 4/2008 | van Hooser et al. | 128/202.27 |
| 2005/0199243 A1 | 9/2005 | Svendsen | |

FOREIGN PATENT DOCUMENTS

| | | |
|---|---|---|
| DE | 40103300.0001 D | 8/2001 |
| DE | 40103300.0002 D | 8/2001 |
| DE | 40103300.0003 D | 8/2001 |
| DE | 40103300.0004 D | 8/2001 |
| EP | 1 208 865 A2 | 5/2002 |
| EP | 0 812 220 B1 | 5/2004 |
| EP | 0 805 694 B1 | 6/2007 |
| FR | 000012046.0001 D | 8/2001 |
| FR | 000012048.0001 D | 8/2001 |
| FR | 000012049.0001 D | 8/2001 |
| FR | 000012050.0001 D | 8/2001 |
| GB | 1 443 152 A | 7/1976 |
| GB | 2 061 465 A | 5/1981 |
| GB | 002100746 D | 8/2001 |
| GB | 002100747 D | 8/2001 |
| GB | 002100748 D | 8/2001 |
| GB | 002100749 D | 8/2001 |
| WO | WO 93/21981 A2 | 11/1993 |
| WO | WO 95/31240 A1 | 11/1995 |
| WO | WO 95/31249 A1 | 11/1995 |
| WO | WO 95/31250 A1 | 11/1995 |
| WO | WO 96/22118 A1 | 7/1996 |
| WO | WO 96/26757 A1 | 9/1996 |
| WO | WO 98/10808 A2 | 3/1998 |
| WO | WO 98/33536 A1 | 8/1998 |
| WO | WO 99/19013 A1 | 4/1999 |
| WO | WO 9919013 A1 * | 4/1999 |
| WO | WO 01/21241 A1 | 3/2001 |
| WO | WO 01/76659 A1 | 10/2001 |
| WO | WO 01/76673 A1 | 10/2001 |
| WO | WO 02/28463 A2 | 4/2002 |
| WO | WO 02/051485 A1 | 7/2002 |
| WO | WO 2004/101044 A1 | 11/2004 |
| WO | WO 2006/133882 A1 | 12/2006 |
| WO | WO 2007/141487 A1 | 12/2007 |

* cited by examiner

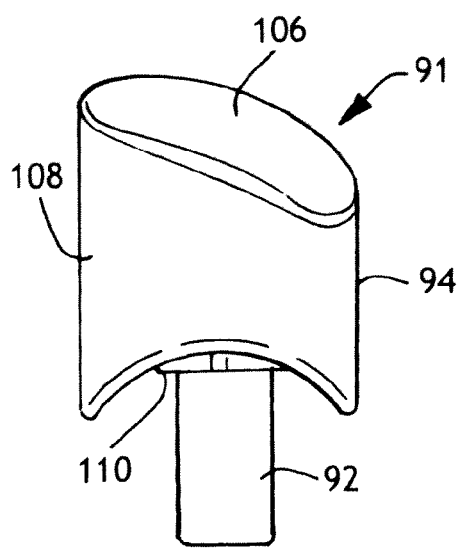
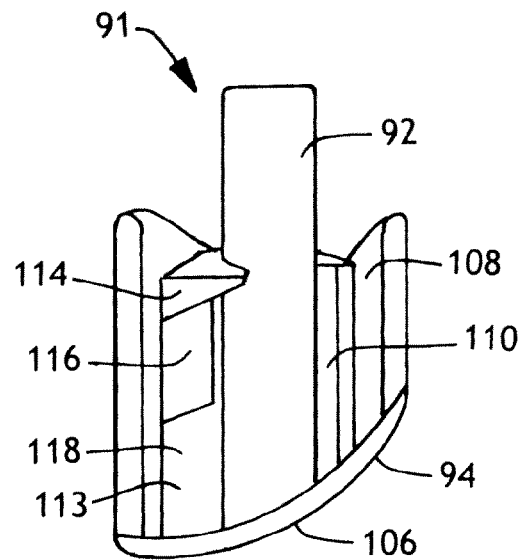
FIG. 9A
FIG. 9B
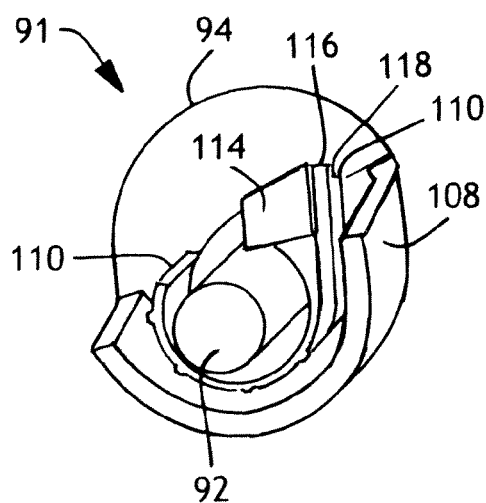
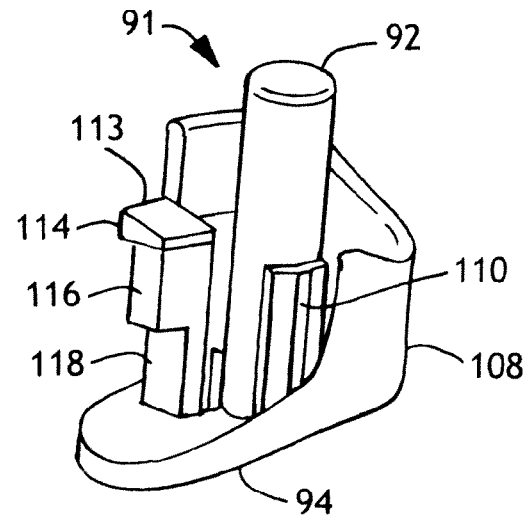
FIG. 9C
FIG. 9D

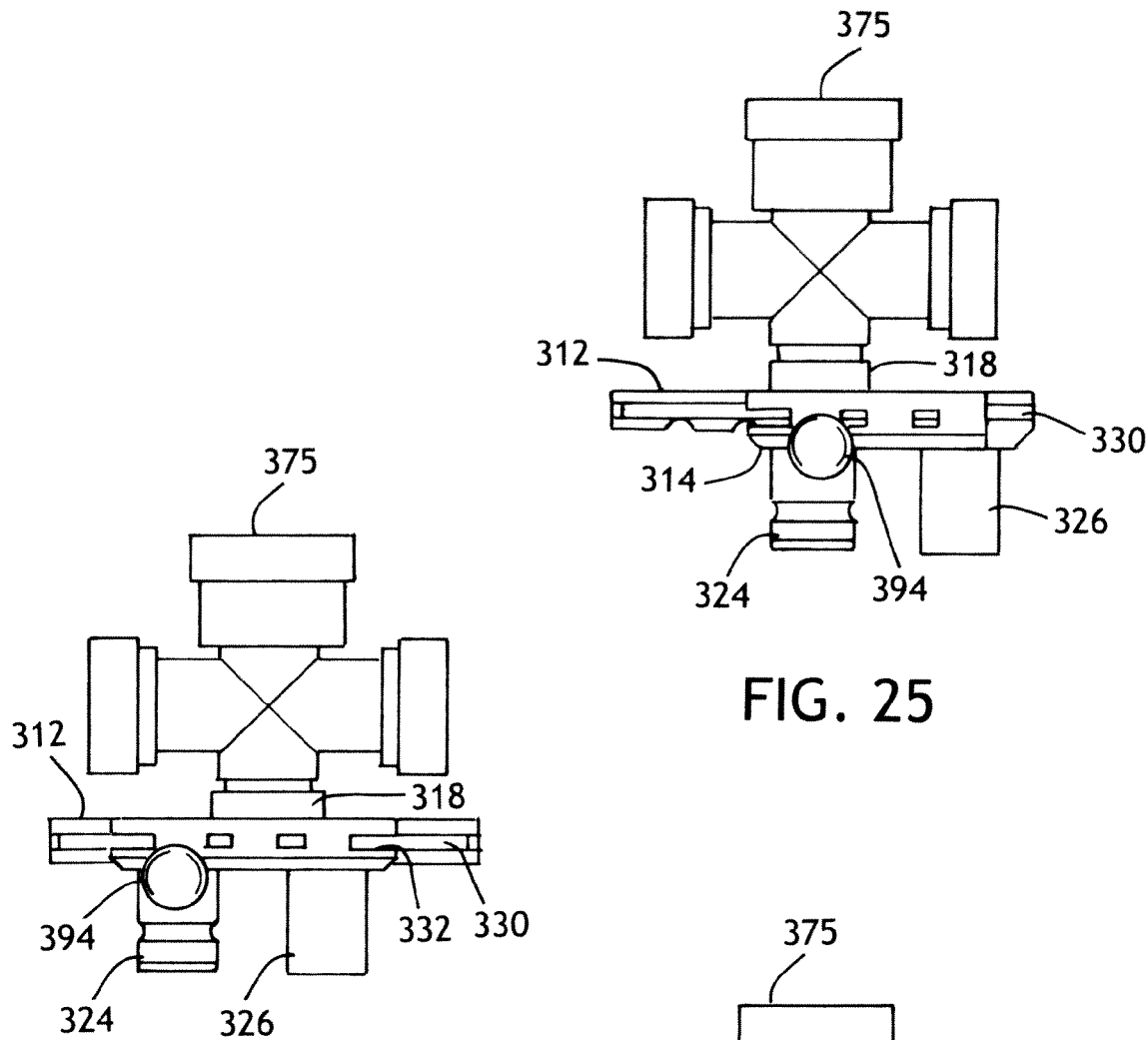
FIG. 25
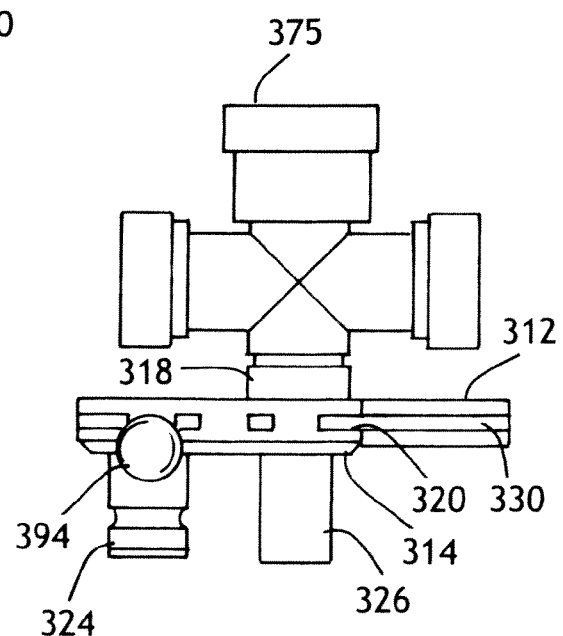
FIG. 26
FIG. 27

RESPIRATORY ACCESS PORT ASSEMBLY WITH PUSH BUTTON LOCK AND METHOD OF USE

CROSS-REFERENCE TO RELATED APPLICATIONS

This application is a continuation-in-part of U.S. Ser. No. 12/333,916 entitled "Rotating Respiratory Access Port Assembly with Push Button Lock and Method of Use" by John Brewer et al., filed Dec. 12, 2008 now abandoned, which is hereby incorporated by reference herein for all purposes.

BACKGROUND

The inventions disclosed herein relate generally to improved medical care for intubated patients, and more particularly to a novel multiple access respiratory port, assembly, manifold, fitting, adaptor, connector and/or access control assembly inventions, and related methods, for ventilating, aspirating, monitoring, sampling, and providing therapeutic delivery to the respiratory tracts of intubated patients, including infants, adolescents, and adults.

Respiratory patient care is a dynamically developing field in medicine, ranging in its needs from infants to the aged. The range of respiratory ailments, both temporary and permanent, to which such patients are subjected, are many and varied. For example, the range of procedures for intubated patients may include the following: ventilation, aspiration, oxygenation, sampling, visual inspection, in-line sensing, pressure monitoring, flushing, medicating and/or lavage. Most problems now center or focus on multiple needs of the patient and accommodation of multiple treatments, some to be performed at the same time. The lack of equipment to facilely, efficiently, and safely accomplish the multiple therapies in the best interest of the patient has been and continues to be a concern.

For example, in low lung capacity patients, such as premature babies and adults suffering from emphysema, one problem is the removal of accumulated lung secretions. It is undesirable to starve such patients of oxygen during the secretion removal process. Secretion removal is accomplished via a suction catheter which is temporarily positioned via a respiratory access assembly in an artificial airway, i.e., an endotracheal tube placed in a portion of the patient's respiratory tract to provide air (oxygen and other gases) to the lungs of such patients.

With these and other patients undergoing respiratory care while intubated, problems may occur, including problems with a respiratory access assembly. Unsafe extended use of a respiratory access assembly for ventilating, aspirating, suctioning and other functions may result in hospital acquired infections, such as, for example, ventilator acquired pneumonia. Also of concern is the reliability of such respiratory access assemblies. Further, the need to open the ventilator circuit to exchange devices and perform other therapeutic treatments is also a concern.

A respiratory access assembly needs to be quickly and easily removed and exchanged without compromising the quality of health care to the patient. Also of concern with a respiratory access assembly is inadvertent conversion from a closed respiratory system to an open respiratory system via malfunction of a respiratory access assembly. Further, stress to the patient caused by inadvertent partial obstruction or occlusion of air passageways in the closed respiratory system to and from the patient's lungs due to malfunction of a respiratory access assembly is a problem. Moreover, dealing with a large inventory of a variety of incompatible components manufactured by different manufacturers which may form the respiratory access assembly is also an issue to the health care provider. Therefore, it would be desirable to have an easy to operate, fail-safe, closed-system respiratory access assembly which provides safe and predictable closed-system access to an intubated patient's respiratory system for multiple purposes, and which has safety features to reduce or eliminate inadvertent damage of the closed respiratory system.

The present invention addresses these needs, providing a respiratory access assembly used in a closed system which includes a safety lock. That is, the present invention substantially alleviates problems which occur with present respiratory access assemblies or devices. The present invention operates in a closed ventilating system and accommodates multiple access to the respiratory system of an intubated patient without compromising the closed circuit character of the system and without interruption of the flow of ventilating gases to the patient. Access to the closed respiratory system through one or more access sites is provided, for example, but not by way of limitation, to ventilate the lungs of the patient with gas or gases, to aspirate secretions from the lungs, to oxygenate the lungs to eliminate or reduce residual carbon dioxide therefrom, to visually inspect selected parts of the patient's respiratory system, to sample sputum and gases, to sense parameters such as flow rates, pressure, and/or temperature, to flush with solution(s), and to administer medication, gases, and/or lavage.

SUMMARY OF THE INVENTION

In response to the difficulties and problems discussed herein, a respiratory access assembly is provided. The respiratory access assembly comprises a distal plate having a port. The port is adapted to be positioned in operable communication with an artificial airway of a patient. The assembly also includes a proximal plate. The proximal plate has a first port and a second port. The distal plate is positioned against the proximal plate in a stacked configuration. Each plate is configured to move. In addition, the assembly includes an actuator positioned adjacent to at least one plate. The actuator cooperates with at least one plate to permit movement of at least one plate when the actuator is positioned in a movement-enabling position. The actuator cooperates with both plates to lock the plates in a fixed position when the actuator is positioned in a locked position, such that the plates are locked into a predetermined position relative to each other. The actuator includes a blocking portion which is configured to extend into at least one port when the actuator is positioned in the movement-enabling position, and to withdraw from the one port when the actuator is positioned in the locked position.

In another aspect of the invention, a respiratory access assembly is provided. The respiratory access assembly comprises a distal plate having a port. The port is adapted to be positioned in operable communication with an artificial airway of a patient. The assembly includes a proximal plate, which has a first port and a second port. The distal plate is positioned against the proximal plate in a stacked configuration. Each plate is configured to move relative to each other. The assembly further includes a closed suction catheter assembly, which has at least a connecting end having an opening provided therein, a suction catheter, and a sleeve positioned over the suction catheter and connected to at least the connecting end. The connecting end is releaseably coupled to the first port. In addition, the assembly includes an actuator positioned adjacent to at least one plate. The actuator cooperates with at least one plate to permit movement of at least the one plate when the actuator is positioned in a movement-enabling position. The actuator cooperates with both plates to lock the plates in a fixed position when the actuator is positioned in a locked position, such that the plates are locked into a predetermined position relative to each other. The actuator includes a blocking portion which is configured to extend into at least one port when the actuator is positioned in the movement-enabling position, and to withdraw from the one port when the actuator is positioned in the locked position. When the actuator is positioned in the movement-enabling position, at least one plate is movable. When the port of the distal plate and the first port of the proximal plate are moved into an alignment, the actuator is positioned into the locked position such that the port of the distal plate and the first port of the proximal plate are axially aligned in a first open position. In this position, the suction catheter is movable through the ports. In addition, in this position, the second port of the proximal plate is positioned in a closed position.

In yet another aspect of the invention, a method of using a respiratory access assembly is provided. The method comprises the step of providing a respiratory access assembly, including a distal plate having a port. The port is adapted to be positioned in operable communication with an artificial airway of a patient. The assembly also includes a proximal plate, which has a first port and a second port. The distal plate is positioned against the proximal plate in a stacked configuration. The distal plate and the proximal plate are configured to move relative to each other. The assembly further includes a closed suction catheter assembly. This closed suction catheter assembly comprises at least a connecting end having an opening provided therein, a suction catheter, and a sleeve positioned over the suction catheter and connected to at least the connecting end. The connecting end is releaseably coupled to the first cuff of the first port. In addition, the assembly includes an actuator positioned adjacent to at least one plate. The actuator cooperates with the plate to enable movement thereof when the actuator is positioned in a movement-enabling position. The actuator cooperates with the plates to lock the plates in a fixed position when the actuator is positioned a locked position, such that the plates are locked together in a predetermined position. The actuator includes a blocking portion which is configured to extend into at least one port when the actuator is positioned in the movement-enabling position, and it is configured to withdraw from the one port when the actuator is positioned in the locked position. The method also includes the step of moving the actuator into a movement-enabling position so that the plates are each movable and simultaneously moving the blocking portion into at least the portion of a port. The method further includes the step of moving at least one plate such that the port of the distal plate and the first port of the proximal plate are in an axial alignment in a first open position. The second port simultaneously is moved into a closed position adjacent the distal plate. Moreover, the method includes the step of moving the actuator into a locked position so that the distal plate and the proximal plate are in a locked position, while simultaneously moving the blocking portion out of the port, thereby opening the port. Finally, the method includes the step of moving the suction catheter through the opened assembly in order to suction secretions from a patient.

DEFINITIONS

As used herein the following terms have the specified meanings, unless the context demands a different meaning, or a different meaning is expressed; also, the singular generally includes the plural, and the plural generally includes the singular unless otherwise indicated.

As used herein, the terms "comprise," "comprises," "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "including," as well as the terms "has", "have", "having" and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the term "port" means an opening into or through a component for the passage of an object and/or a liquid and/or a gas. A port and its cuff may collectively be given the term "port" herein; two ports, each with its associated cuff, may collectively be given the term "ports" herein.

As used herein, the term "cuff" means a generally cylindrical component having an opening therethrough which is positioned over a port and forms a portion of the port. As used herein, the phrase "operable communication" means a transmission or passage for a between two points and/or two structures for a specific purpose. In this example, operable communication would be a passage which permits gasses to pass, and may also be configured to permit objects to pass.

As used herein the term "suction catheter" means long, flexible tubes used to remove secretions from the airway and are available in many sizes, commonly from 5 to 20 French and varying lengths, typically from 15 to 25 inches (38 to 64 cm). Suction catheters may be made from latex and other polymers.

Suction catheters are well known and widely commercially available for many medical uses. Suctioning may be performed using an "open" or "closed" system. In the open system, the suction catheter is merely a flexible plastic tube that is inserted into the flexible lumen with a source of suction connected to the proximal end of the suction catheter. Anything that the suction catheter touches before entering the lumen must be maintained in a sterile condition so a "sterile field" must be created on or next to the patient. The suction catheter must be carefully handled after it is used since it will be coated with the patient's secretions. In contrast, in the "closed" system, for example that disclosed in commonly owned U.S. Pat. No. 4,569,344, a device which may be used to suction secretions is enclosed within a generally cylindrical plastic bag to eliminate or minimize contamination of the suction catheter prior to use. This is generally referred to as a "closed suction catheter" and is available under the tradename TRACH CARE® from BALLARD® Medical Products (Kimberly-Clark Corporation). As the patient requires artificial removal of secretions, the suction catheter may be advanced through one end of the plastic bag, through a connecting fitting and into the flexible lumen. The other, proximal end of the suction catheter is attached to a source of suction. Suction may be applied using, for example, a finger controlled valve on the proximal end of the suction catheter, and the secretions removed. Secretions are thus drawn into the lumen of the suction catheter tube and removed and the system remains closed. The suction catheter is subsequently withdrawn from the flexile lumen and back into the plastic bag to keep the circuit closed. Closed suction systems are generally preferred by healthcare providers since the provider is better protected from the patient's secretions. Closed suction systems are also easier and quicker to use since a sterile field need not be created each time the patient must be suctioned, as is required in open suction systems. The closed suction catheter may be permanently attached to the proximal end of the flexible lumen or may be detachably connected so that it may be replaced periodically.

As used herein, the term and phrase "open" and "open position" and variations thereof, refers to a position of the aligned ports described herein to permit an object, such as a suction catheter, a portion of a bronchoscope, and so forth, move through the aligned ports and into a portion of a patient's respiratory tract.

As used herein, the term and/or phrase "closed" or "closed position" and variations thereof, refers to a position of one or more ports in which the port(s) are not aligned, so that no large object, such as a suction catheter, a portion of a bronchoscope, and so forth, may move through the referenced "closed" port(s). A port may be "closed" or "blocked" such that an object, such as those referenced previously, are blocked or prevented from moving through the port(s). The port may not be totally blocked or closed, however, and gases and/or liquid may, in at least some instances, continued to move through a blocked or closed port.

As used herein, the phrase "suction catheter pathway" includes the components defined herein which are or may be coupled to a suction catheter assembly which, when aligned, provide an opening in an axial alignment to permit a suction catheter to be moved therethrough.

As used herein, the phrase "stationary disk" may refer to either the proximal disk or the distal disk when that disk is grasped by a health care provider and held in a relatively fixed "stationary" position while the opposite disk is rotated to one of the three pre-determined positions by a health care provider. Both disks may be relatively "stationary disks" as well when the disks are positioned and locked together in a fixed, unmoving position.

As used herein, the phrase "rotating disk" may refer to either the proximal disk or the distal disk when the disks are unlocked, so that each may rotate relative to the other. The distal and proximal disks are configured to be positioned in three pre-determined positions. When un-locked, however, both distal and proximal disks are free to rotate relative to each other, and each disk rotates in a direction opposite (up to about 180 degrees or less) relative to each other. Both disks may be "rotating disks" as well when the disks are positioned in the un-locked position so that each disk is free to be rotate in opposite directions by a health care provider.

As used herein, the term "plate" means any shape and configuration of a plate, including, but not limited to, round, square, rectangular, and so forth. The plate may be arced, arched, planar, convex, concave, and so forth.

As used herein, the term "couple" includes, but is not limited to, joining, connecting, fastening, linking, tying, adhering (via an adhesive), or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered.

As used herein, the term "alignment" refers to the spatial property possessed by an arrangement or position of things in a straight line.

As used herein, the terms "orientation" or "position" used interchangeably herein refer to the spatial property of a place where or way in which something is situated; for example, "the position of the hands on the clock."

As used herein, the term "about" adjacent to a stated number refers to an amount that is plus or minus ten (10) percent of the stated number.

These terms may be defined with additional language in the remaining portions of the specification.

BRIEF DESCRIPTION OF THE DRAWINGS

FIG. 9A is a proximal plan view of the button of FIGS. 1 and 2;

FIG. 9B is a distal plan view of the button of FIG. 9A;

FIG. 9C is a side view of the button of FIGS. 9A and 9B;

FIG. 9D is another side view of the button of FIGS. 9A-C;

FIG. 25 is a side view of the respiratory access assembly of FIGS. 22-24, showing the port of the distal plate in an axial alignment with the first port of the proximal plate in an open position (first open position);

FIG. 26 is a side view of the respiratory access assembly of FIGS. 22-24, showing the port of the distal plate positioned between the first port and the second port of the proximal plate in a closed position (all ports closed); and FIG. 27 is a side view of the respiratory access assembly of FIGS. 22-24, showing the port of the distal plate positioned in an axial alignment with the second port of the proximal plate in an open position (second open position).

DETAILED DESCRIPTION OF THE INVENTION

Figure 1:
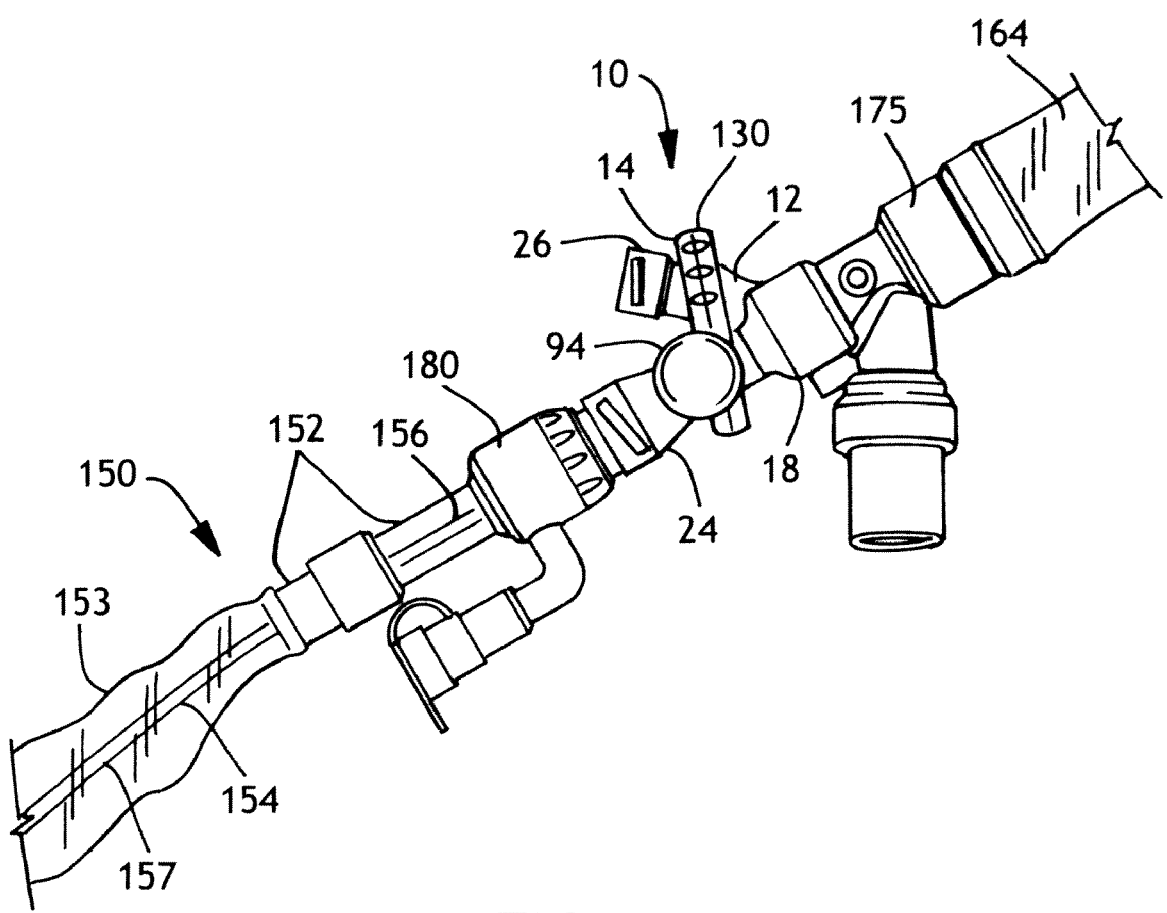
FIG. 1 is a perspective view of the respiratory access assembly of the present invention illustrating the assembly in use and coupled to a respiratory manifold which is attached to an endotracheal tube at a distal end of the assembly, a filter and a suction catheter assembly coupled to a proximal end of the assembly.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Many current designs for respiratory access assemblies may have only one port. In these instances, the suction catheter must be removed when other tasks need to be performed, such as, for example, bronchoscopy, bronchial alveolar lavage, and so forth. Opening a closed ventilating system by removing the suction catheter on such a ventilated patient can lead to infection, as noted previously. Also, current designs of multiple access port manifolds and/or assemblies do not contain a safety lock. In certain instances, due to the lack of such a safety lock, the introduction of a suction catheter through a manifold port may result in a portion of the catheter being guillotined or cut off and aspirated into the patient's lungs. This can lead to significant complications, including airway blockage, infection, and even death. Further, failure to adequately seal a respiratory access assembly may cause a compromise of positive end-expiration pressure (PEEP), which in turn may cause suboptimal ventilation which can result in collapsing alveoli in the patient's lungs. The present invention describes a respiratory access assembly which includes features which permits multiple access without opening the closed ventilation system, and it contains a safety lock feature which prevents loss of any portion of the suction catheter.

The embodiments illustrated and described herein provide three assemblies which are substantially similar. The first and second assemblies describe and illustrate stacked and aligned disks. The third embodiment describes and illustrates stacked and aligned plates. All three embodiments are intended as non-limiting examples.

Figure 11:
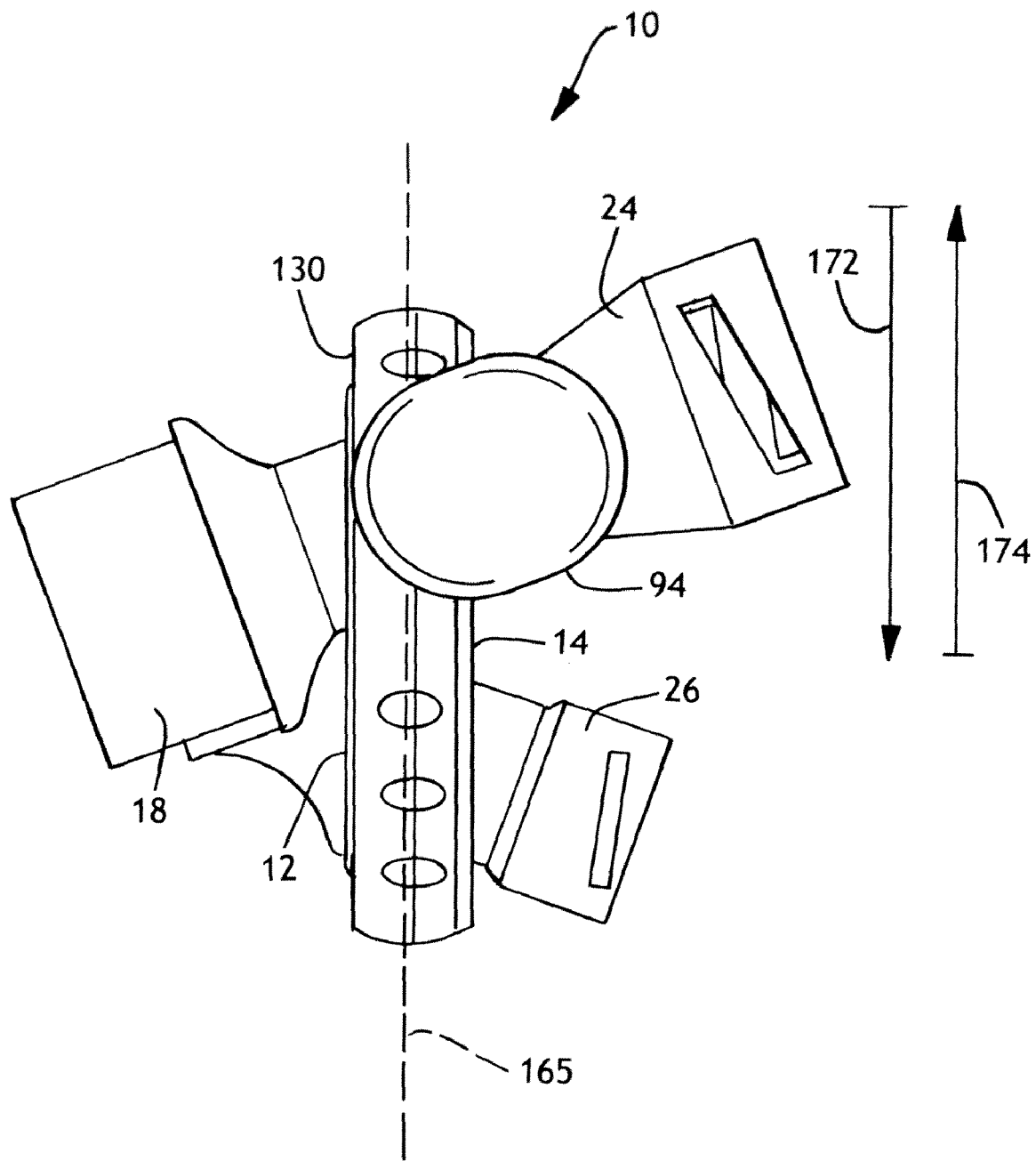
FIG. 11 is a side view of the respiratory access assembly of the present invention, showing the port of the distal disk in an axial alignment with the first port of the proximal disk in an open position (first open position)
Figure 12:
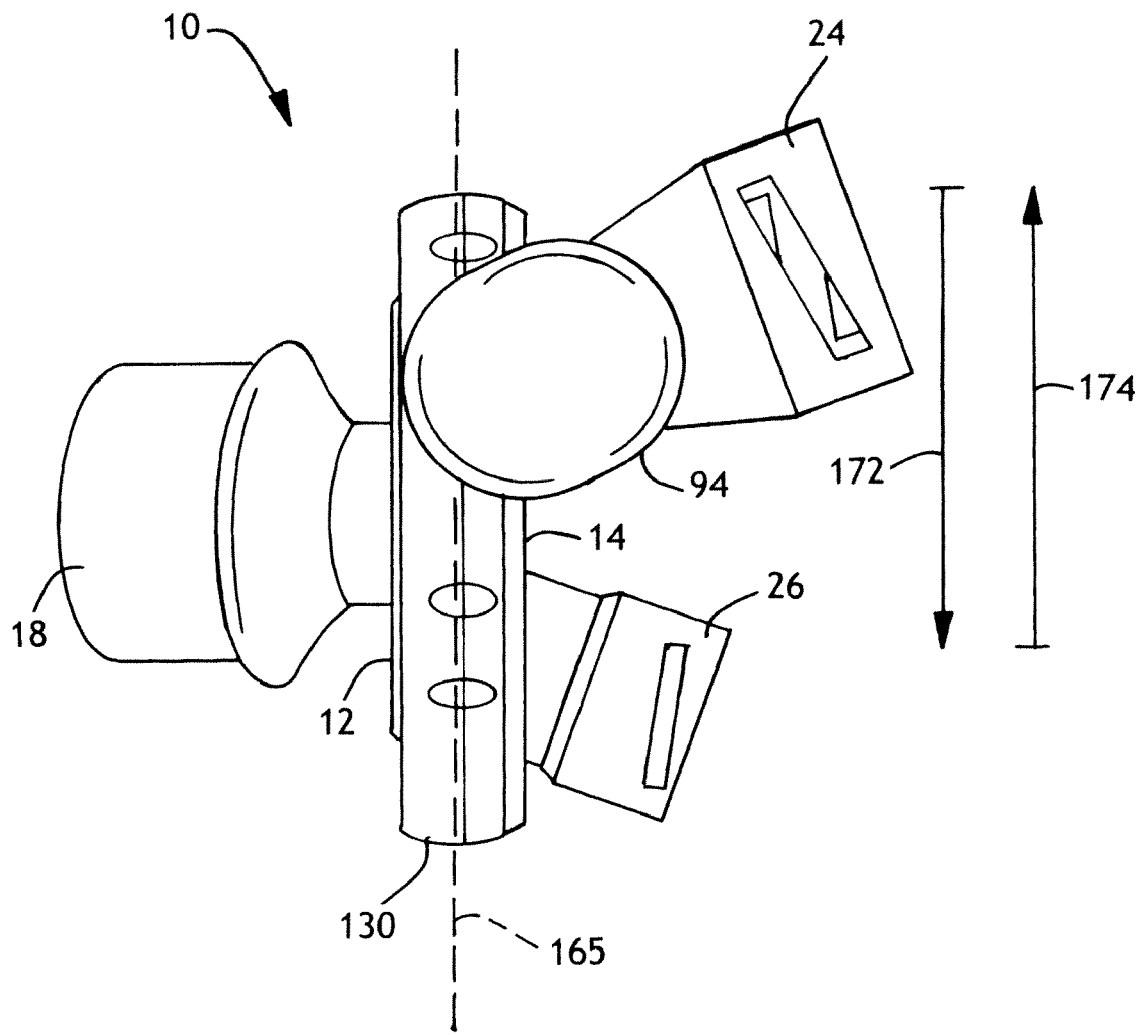
FIG. 12 is a side view of the respiratory access assembly of the present invention, showing the port of the distal disk positioned between the first port and the second port of the proximal disk in a closed position (all ports closed)
Figure 13:
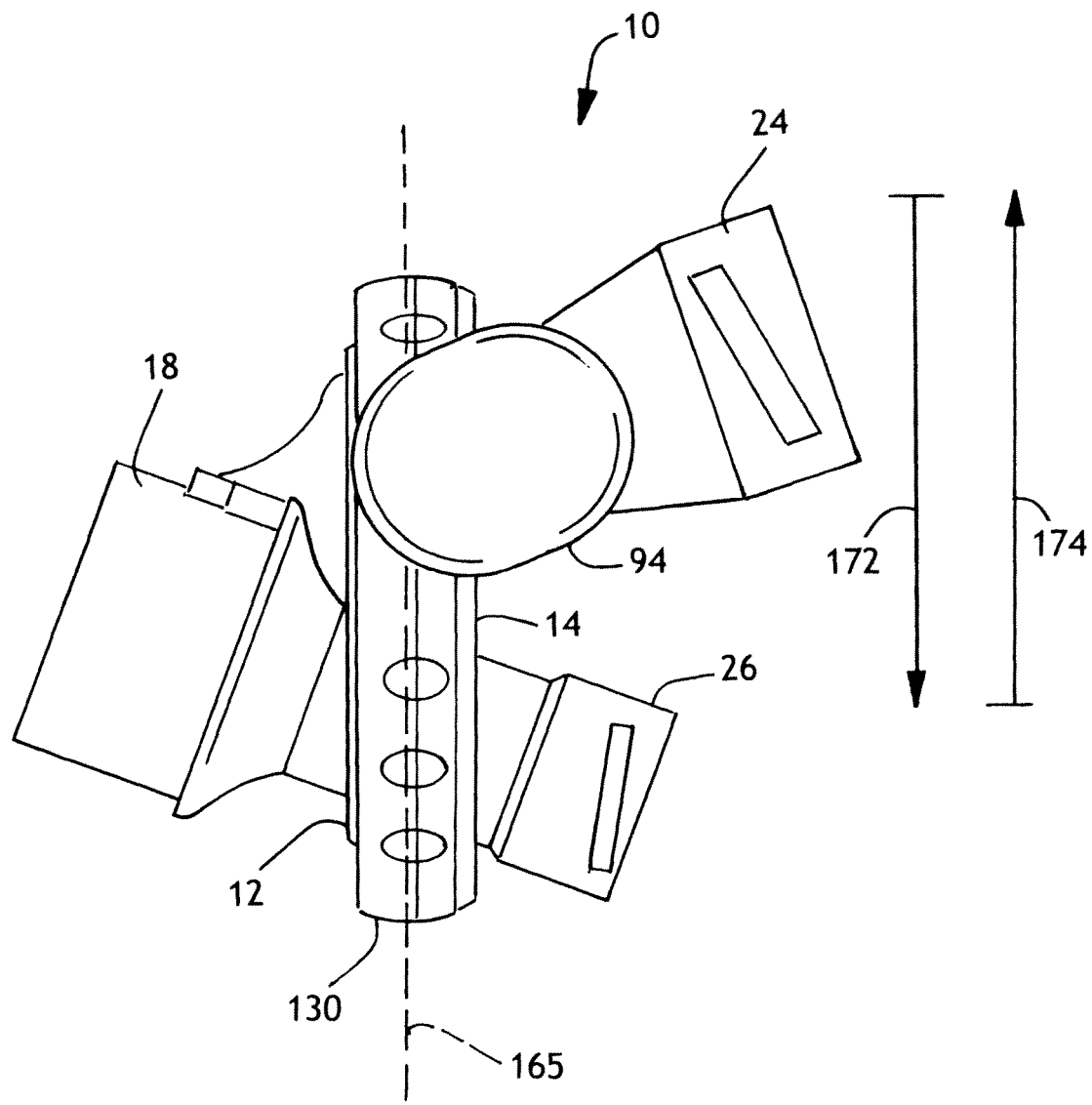
FIG. 13 is a side view of the respiratory access assembly of the present invention, showing the port of the distal disk positioned in an axial alignment with the second port of the proximal disk in an open position (second open position)

Turning now to the drawings, as illustrated in FIGS. 1-15, a rotating respiratory access port assembly 10 is provided. The assembly 10, as shown in FIGS. 1-3, 6-8, 10A-D, and 11-15, includes a distal disk or plate 12 and a proximal disk or plate 14 which are positioned next to each other in a stacked and axially aligned configuration. The distal disk or plate 12 includes at least one angled port 16 whose opening extends through an angled cuff 18 (FIGS. 1-3 and 8). The proximal disk or plate 14 includes a first angled port 20 and a second angled port 22 whose openings each extend through first and second angled cuffs 24, 26, respectively (FIGS. 1, 2, 4, 10A-D, 11-15). When the distal disk or plate 12 is moved or rotated, it provides a position which axially aligns its port 16 with the first port 20 of the proximal disk or plate 14 (FIGS. 11). Alternatively, when the distal disk or plate 12 is moved or rotated it may also provide a position which axially aligns its port 16 with the second port 22 in the proximal disk or plate 14 (FIG. 13). In yet another alternative, when the distal disk or plate 12 is moved or rotated, it may also provide a position in which its port 16 is not aligned with either the first port 20 or the second port 22. In each instance, when one set of ports align axially, the opposite port on the proximal disk or plate 14 will be blocked by a portion of the distal disk or plate 12. In this position, the ports 16, 20 and 22 are blocked by a portion of one of the disks or plates 12 or 14 in a closed position and none are aligned (FIG. 12).

Figure 2:
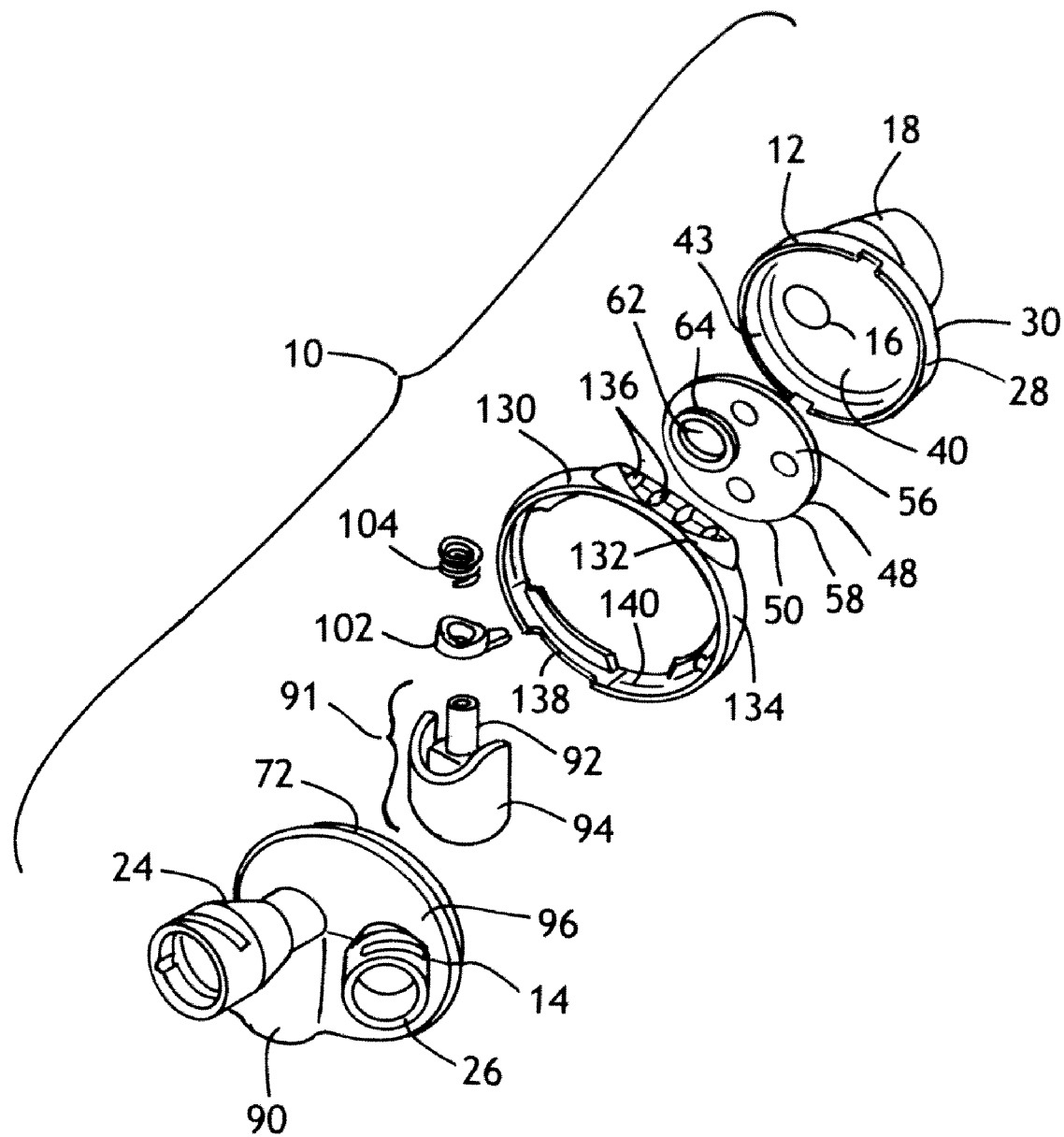
FIG. 2 is an exploded perspective view of the respiratory access assembly of FIG. 1.
Figure 3:
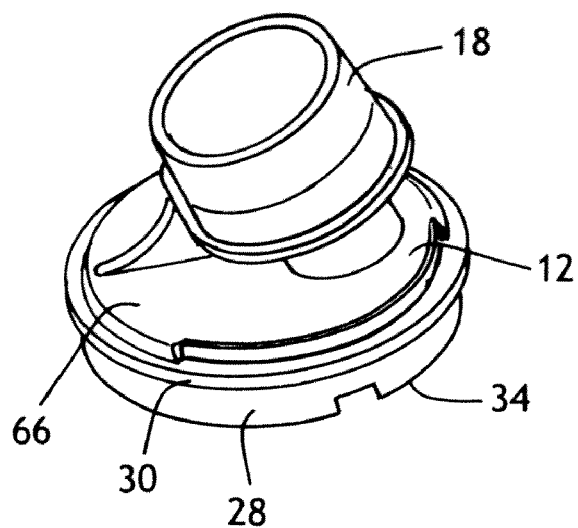
FIG. 3 is a perspective view of a distal disk of FIGS. 1 and 2.
Figure 4:
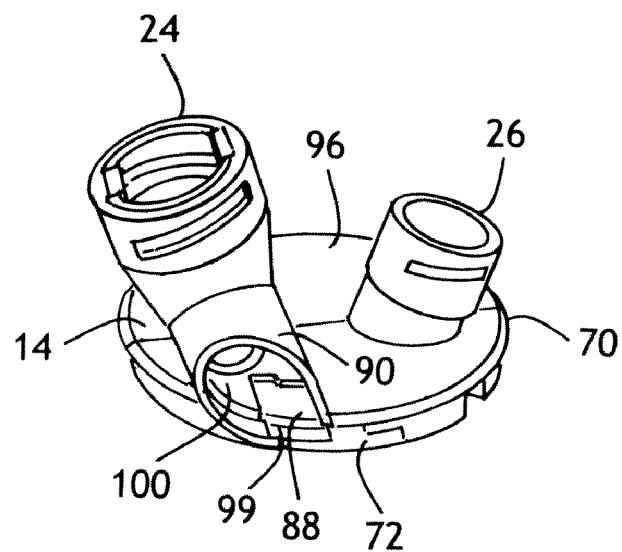
FIG. 4 is a perspective view of a proximal disk of FIGS. 1 and 2.
Figure 5A:
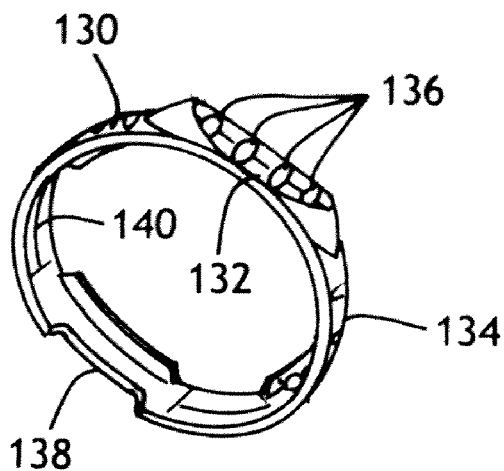
FIG. 5A is a perspective view of a collar of FIGS. 1 and 2; showing a thumb landing area.
Figure 5B:
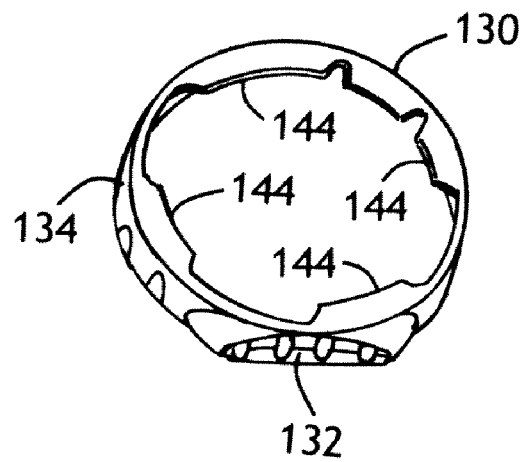
FIG. 5B is a perspective view of the collar of FIG. 5A, but showing a plurality of flanges.
Figure 5C:
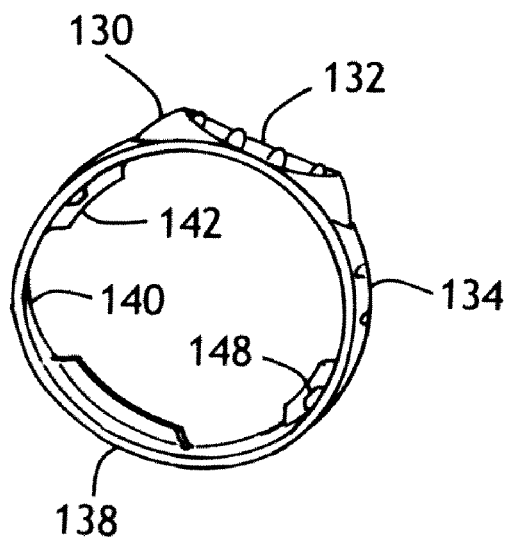
FIG. 5C is a perspective view of the collar of FIGS. 5A and 5B, but showing a pair of tabs on an inner surface.
Figure 6:
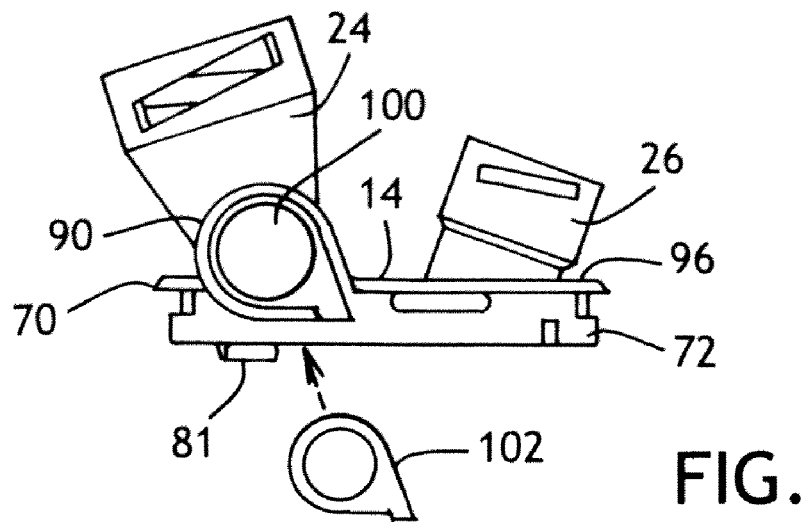
FIG. 6 is a side view of the proximal disk of FIG. 4.
Figure 7:
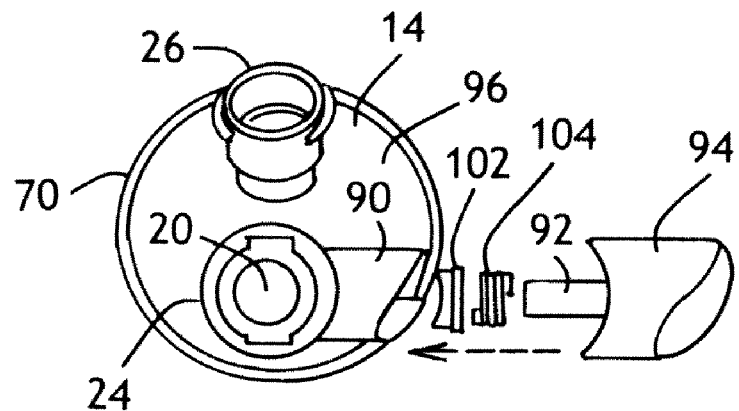
FIG. 7 is a plan view of a proximal surface of the proximal disk of FIGS. 6 and 7, showing a button, a spring and an O-ring.
Figure 8:
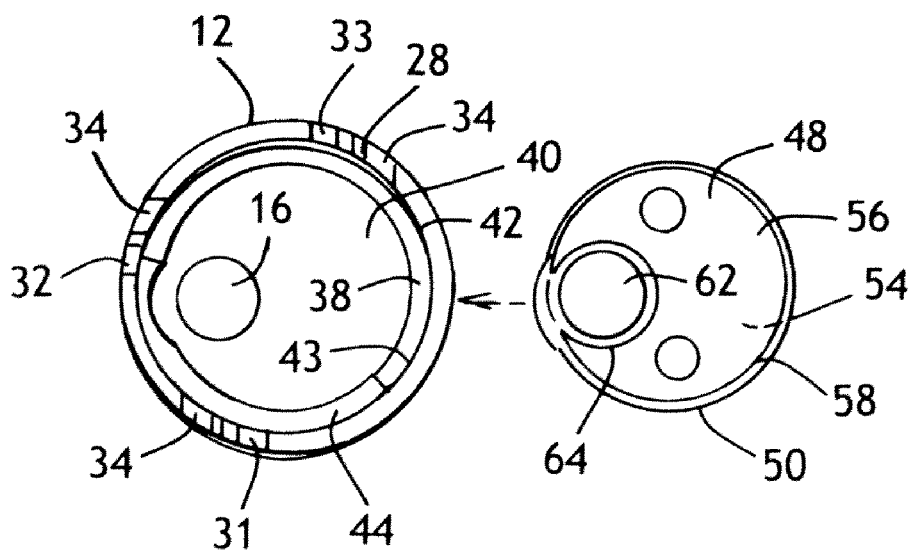
FIG. 8 is a plan view of a proximal surface of the distal disk of FIG. 3, and showing a seal which is desirably positioned on the proximal surface.
Figure 10A:
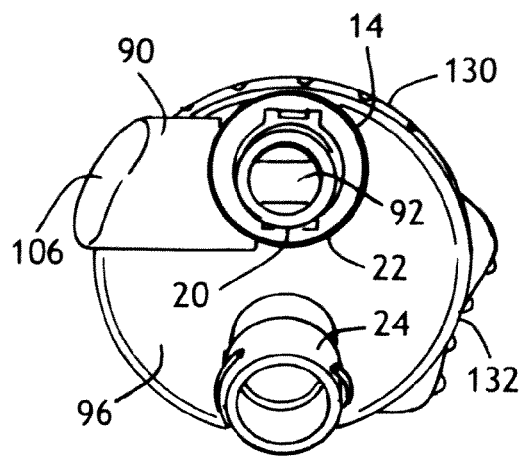
FIG. 10A is a plan view of the proximal surface of the proximal disk of FIGS. 1, 2, 4 and 6, but showing the button in a pressed-in (movement-enabling) position, a plunger of the button blocking a first port.
Figure 10B:
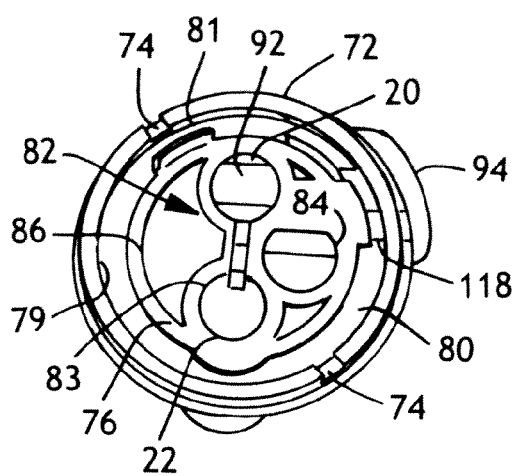
FIG. 10B is a plan view of the distal surface of the proximal disk of FIG. 10A.
Figure 10C:
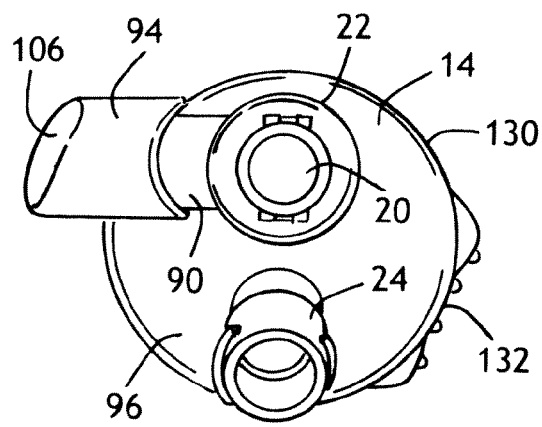
FIG. 10C is a plan view of the proximal surface of the proximal disk of FIG. 10A, but shown the button in a moved out (locked) position, the plunger moved out of the first port.
Figure 10D:
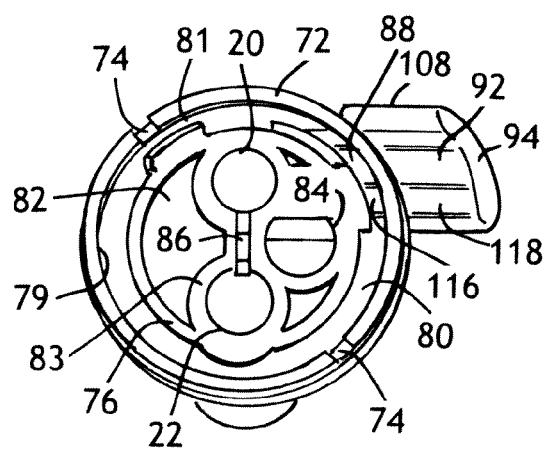
FIG. 10D is a plan view of the distal surface of the proximal disk of FIG. 10D.

The distal disk 12 also desirably includes a lip 28 positioned on an outer edge 30 of the disk 12, as illustrated in FIGS. 2, 3 and 8. The lip 28 may include three notches, that is, a first notch 31, a second notch 32 and a third notch 33 about the lip 28. The three notches, 31, 32 and 33 cooperate with other components to provide three pre-determined positions in which the disks 12, 14 releasably lock together. A plurality of ramps (collectively "34") may also be provided on the lip 28 adjacent each first, second and third notch 31, 32, and 33. The ramps 34 desirably provide mechanical stability and strength against bending forces. In addition, the ramps 34 may provide clearance for a spring and/or a plunger provided with a button, described in greater detail below. A groove 38 may desirably be provided on at least a portion of a proximal surface 40 of the distal disk 12 adjacent a junction 42 of the lip 28 and the edge 30 of the distal disk 12. The groove 38 desirably follows a portion of the inner periphery 43 of the distal disk 12. Alternatively, however, no groove may be formed in the disk 12 (not shown). A rib 44 is desirably provided, and it also extends around a portion of the inner periphery 43 of the distal disk 12. Alternatively, a pair of stop tabs may also be used in place of the rib (not shown). These components cooperate with components of the proximal disk 14, described in detail below, to permit rotation of the distal and proximal disks 12, 14. A flexible polymer elastomeric seal 48 is also desirably provided on the proximal surface 40 of the distal disk 12. The seal is used to maintain the closed ventilation system seal between the distal and the proximal disks 12, 14.

The seal 48, as shown in FIGS. 2 and 8, also is desirably disk-shaped, and it has a perimeter which is slightly smaller than a perimeter of the inner periphery 43 of the distal disk 12. The seal 48 is substantially flat on its distal surface 54, but on its proximal surface 56, the seal 48 has a perimeter rib 58 extending about its perimeter 50. Similarly, the seal 48 has an opening 62 formed therethrough which is configured, but not by way of limitation, to conform to the configuration of at least the port 16. Desirably, however, the opening 62 also at least substantially conforms to the first port 20 and the second port 22. A port rib 64 is formed about the opening 62 on the proximal surface 56 of the seal 48. The perimeter rib 58 and the port rib 64 cooperate with components on a distal surface 65 of the proximal disk 14 to create a seal therebetween, as will be described in detail below. It will be understood that when the seal 48 is positioned centrally on the proximal surface 40 of the distal disk 12, the perimeter rib 58, a portion of the proximal surface 40 of the distal disk 12 and its lip 28 may cooperate to provide the groove 38 (not shown).

The distal disk 12 includes the cuff 18 formed about the port 16 on a distal surface 66 thereof (FIG. 1-3). The cuff 18 desirably is configured to releaseably couple to a connector or a manifold 175 which is coupled to or forms a portion of an artificial airway. This connection may be made, for example, by frictional rotational, leur lock, interlocking tabs, threaded components, and so forth.

The proximal disk 14 (FIGS. 1, 2, 4, 6, 7 and 10A-D) includes a distal surface 68 and an outer edge 70. An outer lip 72 is formed adjacent or near the outer edge 70 and is configured to cooperatively overlap the lip 28 of the distal disk 12. The outer lip 72 has more than one notch, and desirably may include two notches (collectively "74") formed therein. An inner rib 76 is formed a short distance interiorly relative to the outer lip 72 on the distal surface 68 of the proximal disk 14. The inner rib 76 does not extend in a complete circle about an inner periphery 79 of the outer lip 72. The short distance defines a rotating groove 80 configured to accept the lip 28 of the distal disk 12. A tab 81 is provided on the inner rib 76 which acts a stop tab 81.

In operation, the lip 28 of the distal disk 12 fits in the groove 80 in between the outer lip 72 and the inner rib 76 of the proximal disk 14 (FIGS. 8 and 10A-D). The tab 81 of the proximal disk 14 cooperatively fits within the groove 38 of the distal disk 12, thereby permitting the distal disk 12 to rotate within the confines of the groove 38 relative to the proximal disk 14. The rib 44 of the distal disk 12 also acts as a stop, thereby preventing continuous rotation of the distal disk 12. Further, these components prevent over-rotation which would likely result in kinking of any suction catheter position through the rotating access port 10. Turning back to the proximal disk 14, perimeter ribs 82, 83 are formed about the periphery of the first and second ports 20, 22. In between the first and second ports 20, 22, a generally D-shaped portion 84 is provided, and is used in providing a closed position, which will be described in further detail below. A channel 86 may be provided which connects and extends between the two perimeter ribs 82, 83. The channel permits the first and second ports 20, 22 to be in both gaseous and fluid communication with each other. However, it will be appreciated that the proximal disk 12 may be formed without a channel between the first and second ports 20, 22 as well (not shown). An opening 88 is formed through a portion of the rotating groove 80. The opening 88 extends into a button housing 90 and it is configured to at least partially contain an actuator or button assembly 91 including a blocking portion or plunger 92 and a button 94 (FIGS. 4, 6, 7 (A-D and 10A-D).

The button housing 90 is formed from a portion of a proximal surface 96 of the proximal disk 14. The proximal surface 96 includes first and second cuffs 24, 26 which surround the first and second ports 20, 22, respectively. Each first and second port 20, 22 and its respective first and second cuff 24, 26 are provided, as noted previously, at an angle relative to the stacked distal and proximal disks 12, 14.

At least a portion of the button housing 90 may be formed, but not by way of limitation, to intersect the first cuff 24 of the first port 20 at about, but not by way of limitation, a 90 degree angle. The housing 90 may be formed, for example, semi-cylindrically (that is, for example, but not by way of limitation, generally C-shaped or U-shaped) to accommodate the configuration of the button assembly 91 and the button 94 and plunger 92 integrally formed therewith or coupled thereto (FIGS. 4, 6, 7 and 10A-D). The button housing 90 is also desirably formed to include a side opening 100 in a portion of the outer lip 72 of the proximal disk 12, which also is in an open communication with the opening formed through the first cuff 22. The proximal disk 14 includes a notch or divot 99 in the outer lip 72; a portion of the button 94 contacts the divot 99 in order to hold the button 94 to the distal and proximal disks 12, 14. The divot 99 is formed to communicate with the side opening 100 in the first cuff 24 of the first port 20. A flexible, polymer elastomeric O-ring 102 is desirably positioned next to an inner perimeter of the side opening 100. The O-ring 102 provides a seal for the plunger against PEEP pressure loss and a landing area for a spring 104 which may desirably be constructed of metal, plastic, or any combination thereof. The spring 104 is positioned over the plunger 92 and extends between the O-ring 102 and the button 94, biasing the button 94 and plunger 92 outward. The spring 104 comprises a coiled spring, however, other non-coiled springs and biasing devices may be used.

The button 94, as illustrated in FIGS. 9A-D, may also desirably include a thumb landing area 106 and an outer shell 108 which substantially follows the configuration of the button housing 90, and which is therefore generally C-shaped or U-shaped. The button 94 also includes an inner shell 110 of similar C or U-shaped configuration which is spaced a short distance from the outer shell 108. The plunger 92 is coupled to an inner surface (not shown) of the thumb landing area 106 and it is positioned a short distance away from the inner shell 110. The button housing 90 is desirably stacked or positioned between the respective outer and inner shells 108, 110 in order to hold the plunger 94 in a position to extend from the housing 90 into the side opening 100, thereby blocking the first port 22 in its first cuff 24 (FIGS. 7 and 10A-D). In addition, the perimeter edge 113 of the inner shell 110 includes a holding tab 114, a locking tab 116, and a movement-permitting portion 118, which operates to permit movement of the button 92 and the plunger 94 in order to both move and releaseably lock the button and plunger 94 in a plurality of predetermined positions.

The holding tab 14 is configured to hold the button 94 in a coupled position against the distal and proximal disks 12, 14 (FIGS. (A-D and 10A-D). The holding tab 14 contacts the lip 28 of the distal disk 12, and will not permit the button 94 to move away from the stacked disks 12, 14, even though the spring 104 biases the button 94 outward, away from the disks 12, 14. The locking tab 116 is configured to fit within and contact each of the first, second and third notches 31, 32, or 33, respectively, on the lip 28 of the rotary disk 12. When the locking tab 116 is positioned to contact the lip 28 via the notches 31, 32, or 33, the locking tab 116 locks or prevents rotation of the distal disk 12 relative to the proximal disk 14. The movement permitting portion 118 is configured to extend below the lip 28 of the distal disk 12. In this position, the locking tab 116 is positioned against the inner periphery 43 of the distal disk 12. Therefore, the locking tab 116 is disengaged and un-locked from the distal disk 12, permitting the distal disk 12 to rotate within the confines previously described (i.e. about 180 degrees or less) of the proximal disk 14. The movement-permitting portion 118 only permits movement when a user depresses the button 94 inward, toward the disks 12, 14 and holds the button 94 in the depressed position while starting the rotation of the distal disk 12. In this manner, the locking tab 116 is positioned in the locked position and the blocking portion or plunger 92 is extended via the side opening 100 into the first cuff 24 of the first port 20, thereby effectively blocking the first port 20 and preventing the passage of a suction catheter therethrough. The plunger 92 remains in the first port 20 until the distal disk 12 is rotated such that one of the first, second and third notches 31, 32, and/or 33 crosses the movement-permitting portion 118. The first, second or third notches 31, 32, or 33 provide sufficient space to permit the outward movement of the perimeter edge 113, thereby permitting outward movement of the spring-biased plunger 92 and button 94 away from the outer edges 30, 70 of the distal and proximal disks 12, 14 such that the locking tab 116 is moved outward into a position in one of the notches 31, 32, or 33 to block the rotation of the distal disk 12 and thereby lock the distal disk 12 into a fixed, non-moveable position. In this position, the plunger 92 is again positioned away from the opening through the first port 20 and/or first cuff 24, and it moves back into the button housing 90 thereby un-blocking the first port 20.

The distal disk 12, its seal 48, the proximal disk 14, the spring 104, the O-ring 102 as well as the button assembly 91 cooperate together to define three pre-o determined positions of the assembly 10. The first position, as shown in FIG. 11, defines an opened position (a first open position) of the port 16 and cuff 18 aligned with the first port 20 and first cuff 24, such that an axial alignment and communication is created through the aligned ports 16, 20 and cuffs 18, 24, respectively. The seal 48 and its respective ribs 58, 64 positioned on the distal disk 12 act to seal and maintain the secretions substantially within the assembly 10 and the closed circuit ventilation system such that PEEP may be maintained. In the first position, the seal 48 and the proximal surface 40 of the distal disk 12 also provide a closure to the second port 22, which may also have a cap (not shown) which provides a closure to the cuff 26.

The second position, as illustrated in FIG. 12, defines a closed position of the port 16 relative to the first and second ports 20, 22, in that the distal disk 12 is rotated to a position between first and second ports 20 and 22. The seal 48 then assists in sealing all ports 16, 20, 22 closed. Notably, in this position, the port 16 and its cuff 18 of the distal disk 12 are out of an axial alignment with either the first port 20 or the second port 22. The first and/or second cuffs 24, 26 may also have a cap (not shown) to provide a closure over each cuff 24, 26. Alternatively, one cuff 24 or 26 may have a suction catheter assembly or other device coupled thereto which provides a closure.

The third position, as shown in FIG. 13, defines an opened position (a second open position) of the port 16 and cuff 18 of the distal disk in axial alignment with the second port 22 and second cuff 26 of the proximal disk 14. In this position, an axial alignment and operable communication is created through the ports 16, 22 and cuffs 18, 26. The seal 48 and its respective ribs 58, 64 positioned on the distal disk 12 acts to seal and maintain the secretions substantially within the assembly 10 and the closed circuit ventilation system such that PEEP may be maintained. In this third position (second open position), the seal 48 and the proximal surface 40 of the distal disk 12 also provide a closure to the first port 20, which may also have a cap for closure (not shown) or an attached suction catheter assembly or other device (not shown) which acts to provide a closure.

The assembly 10 also may include a round collar 130, as illustrated in FIGS. 1, 2, 5A-C and 11-15. The collar 130 may include a thumb landing 132 on an outer perimeter surface 134 which may have a plurality of ribs 136 to enhance a user's grip thereon. The collar 130 may also have a cut-away portion 138 to accommodate the button housing 90 and button assembly 91. The collar 130 may include, on an inner surface 140, a pair of tabs 142 which cooperate with the two notches 74 in the outer lip 72 of the proximal disk 14 to hold the collar 130 in a position about the disks 12, 14. The collar 130 may also include a plurality of flanges 144 which are desirably positioned substantially perpendicular to the collar 130 and which may be positioned over a portion of a distal surface 65 of the distal disk 12 and configured to assist in holding the distal disk 12 in a rotating position relative to and against the proximal disk 14. The collar 130 may be held in a lock-tab position against the distal and/or proximal disks 12, 14, or, alternatively, the collar 130 may be partially adhered to the proximal disk 14. Further, the collar 134 may be frictionally fit about the proximal disk 14. However, it will be appreciated that the assembly 10 may be formed without a collar 130, and may be connected together by adaptation of, for example, but not by way of limitation, an outer edge of the proximal disk 14, the distal disk 12, or both (not shown).

A suction catheter assembly 150, as illustrated in FIG. 1, includes at least a distal end connector 152 which desirably releaseably couples to the first cuff 24 of the first port 20 of the proximal disk 14 (not shown). Alternatively, the suction catheter assembly may be coupled to an intermediate quick release connector 180 which is releaseably coupled to the first cuff 24, as illustrated in FIG. 1. A sleeve 153 is desirably coupled to the distal end connector 152 and extends at least substantially over a suction catheter 154 and may include a proximal end connector (not shown) to substantially cover the suction catheter 154. The suction catheter 154 includes a distal tip 156 with at least one opening (not shown) therein. The suction catheter 154 also includes an elongated body 157 having a lumen therethrough and an open proximal end (not shown). The proximal end of the suction catheter 154 is adapted to couple to at least a portion of a suctioning apparatus (not shown) which provides a suctioning force to the suction catheter 154. It will be appreciated that the suction catheter 154 has a length which is sufficient to extend through the assembly 10 and through any attached connector or manifold 175 and through an endotracheal tube or artificial airway 164 and into a portion of a patient's respiratory tract in order to suction secretions therefrom. When the suction force is discontinued, the suction catheter 154 is then desirably withdrawn from the patient's respiratory tract and/or artificial airway 164 and the assembly 10 and it is returned to its sleeve 153. In this manner, the length of the suction catheter 154 is contained within the sleeve 160 and it is therefore positioned outside of the closed circuit ventilation system of the patient until needed again for suctioning secretions.

The angle of the port 16 and its cuff 18 of the distal disk 12 and the first and second ports 20, 22 and their respective first and second cuffs 24, 26 may be any angle, so long as when the port 16 and its cuff 18 are aligned with the first port 20 and its first cuff 24, the ports 16, 20 and cuffs 18, 24 cooperate to provide an axial alignment. Similarly, when the port 16 and its cuff 18 of the distal disk 12 are aligned with the second port 22 and the second cuff 26, the ports 16, 22 and cuffs 18, 26 cooperate to provide an axial alignment. Further, in each of these respective alignments, it will be appreciated that these components of the assembly 10 are substantially axially aligned with at least the proximally coupled external components of a patient's artificial airway. Such an axial alignment is desirable in order to prevent kinking or inadvertent crimping of a suction catheter passed through the ports 16, 20, 22 and their respective cuffs 18, 24, 26. This is because a suction catheter is formed of a light weight and flexible material which is prone to overlapping, folding, kinking and/or crimping when forced to pass through turns, thereby affecting its ability to suction.

When positioned in the first position (first open position), the first port 20 and first cuff 24 of the proximal disk 14, as shown in FIG. 11, are positioned desirably at an angle of about 35 to about 55 degrees relative to an axis 165, which is in a parallel alignment with at least a portion of each surface of the distal disk 12 and the proximal disk 14. The port 16 and its cuff 18 of the distal disk 12 are desirably positioned at an angle of about 215 to about 235 degrees. It will be appreciated, however, that relative to each other, the first port 20 and first cuff 24 and the port 16 and its cuff 18 cooperate together to provide an angle of about 180 degrees when positioned in the opened first position, through which a suction catheter 154 may be positioned.

In the first position, the second port 22 and its second cuff 26 of the proximal disk 14 (FIG. 11), are desirably positioned at an angle of about 125 to about 145 degrees relative to the axis 165 positioned through the disks 12, 14, as shown in FIGS. 11-13. However, when the port 16 and its cuff 18 of the distal disk 12 are rotated into a third position (FIG. 13) (second open position) relative to the second port and second cuff 22, 26, the port 16 and its cuff 18 are positioned at an angle of about 305 to about 325 degrees relative to the axis 165. It will be appreciated that the second port 22 and the second cuff 26 and the port 16 and its cuff 18 cooperate together to provide an angle of about 180 degrees when positioned in the third position (second open position), creating an open position through which an instrument, such as, for example only, a portion of a bronchoscope, a portion of a catheter, and so forth, may be positioned.

In the closed second position (third position or closed position), the port 16 and cuff 18 of the distal disk 12 are moved into a position out of alignment with both the first port 20 and the second port 22. The port 16 and cuff 18 of the distal disk 12 are positioned at about a 90 degree angle relative to the axis 165. However, as seen in FIG. 12, the port 16 and its cuff 18 are positioned in another axis (not shown) relative to axis 165.

Figure 14:
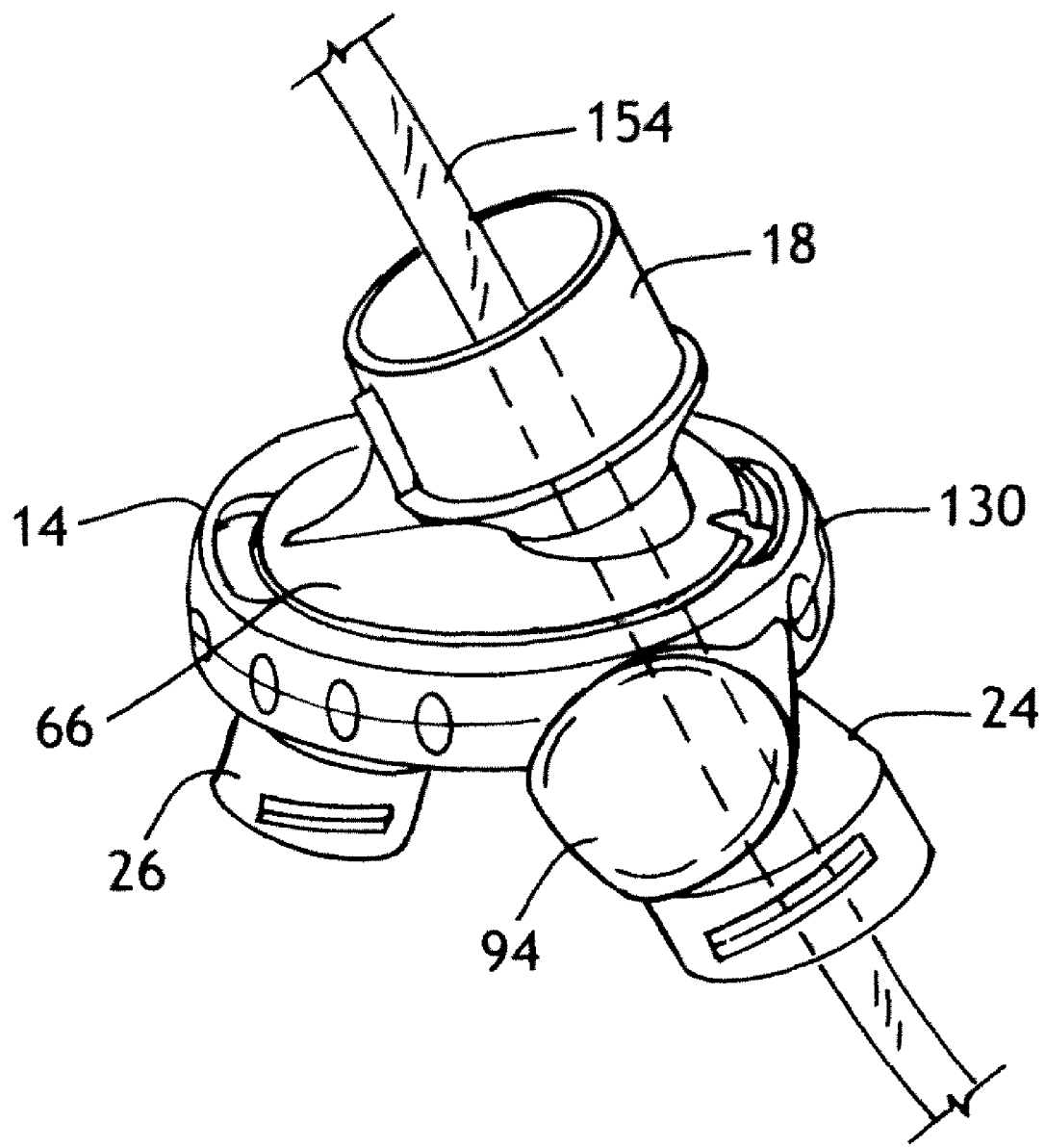
FIG. 14 is a perspective view of the respiratory access assembly of the present invention as shown in FIGS. 1 and 11-13, showing a suction catheter positioned therethrough.
Figure 15:
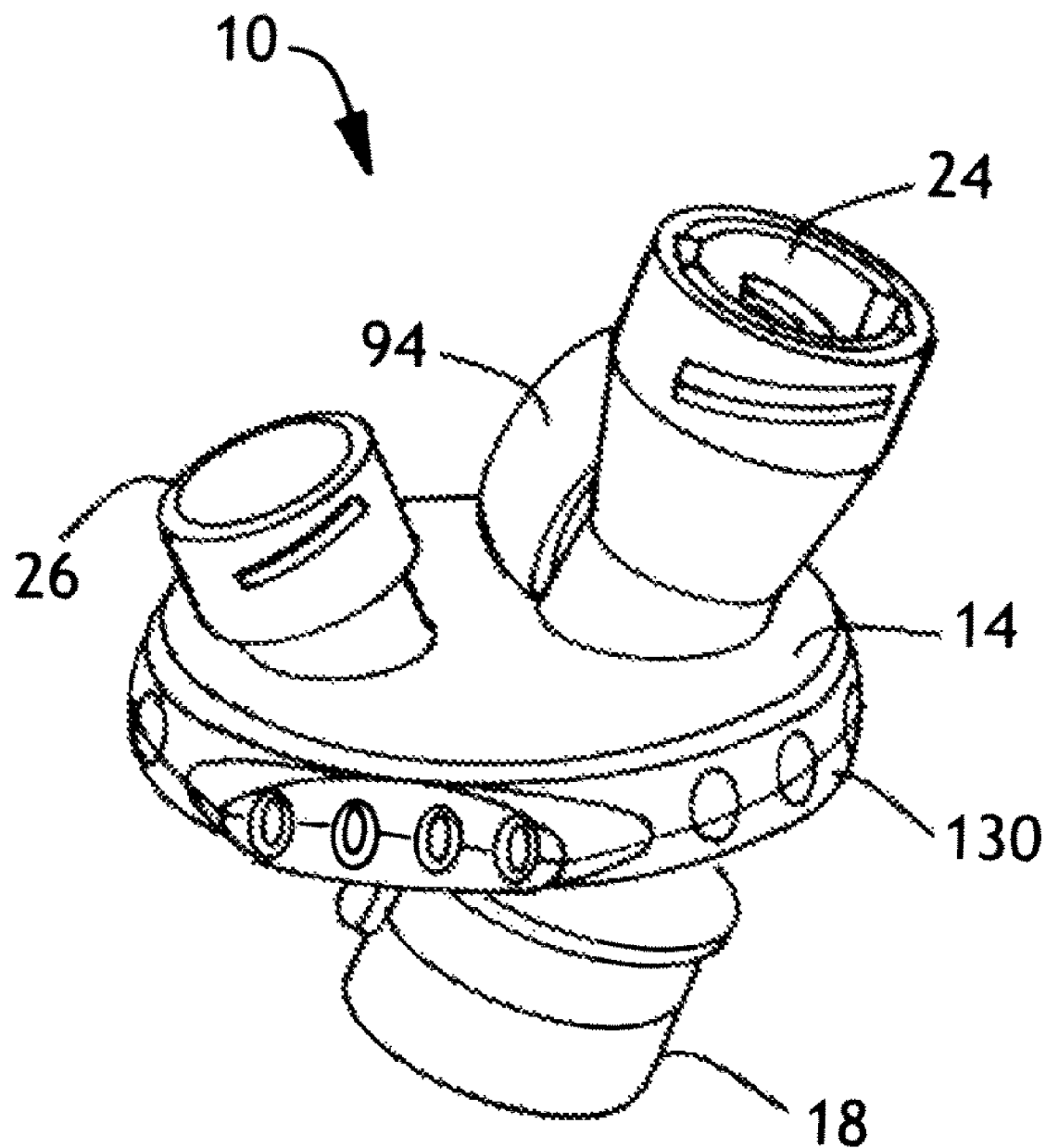
FIG. 15 is another perspective of the respiratory access assembly of the present invention as illustrated in FIGS. 1 and 11-13.

In a method of use, the assembly 10 is desirably indirectly coupled via a manifold 175 or directly coupled (not shown) to an artificial airway 164 of a patient. And, for this example, but not by way of limitation, the assembly 10 is positioned in one of the plurality of predetermined positions, namely, the first position, to enable the passage of the suction catheter 154 through the assembly 10 in order to suction and remove secretions from the patient's artificial airway and respiratory tract, as illustrated in FIGS. 11 and 14. In this first position, the port 16 and the cuff 18 of the distal disk 12 are positioned in an axial alignment with the first port 20 and first cuff 24 of the proximal disk 14. The locking tab 116 on the perimeter edge 113 of the button assembly 91 is desirably positioned through the first notch 31 of the distal disk 12, thereby holding the distal disk 12 and the proximal disk 14 together in the fixed position. In this position, the plunger 92 is positioned in the button housing 90, and it is not blocking any portion of the first port 20 or first cuff 24. Therefore, ports 16, 20 and cuffs 18 and 24 are aligned so that the assembly 10 is in operable communication with the artificial airway 164 and the respiratory tract of the patient, and the suction catheter 154 desirably is moved through the opened position of the assembly 10, i.e., the suction catheter pathway 166, and into the artificial airway and/or respiratory tract of a patient for suctioning secretions therefrom.

When the button 94 of the button assembly 91 is pushed, or depressed, the button only depresses very slightly because the plunger 94 is prevented from entering the opening in the first port 20 through the side opening 100 in the first cuff 24 due to the presence of the suction catheter 154 positioned through the ports 16, 20 and cuffs 18, 24. Since the button 94 cannot be pushed completely inward, the distal disk 12 cannot be disengaged from the locking tab 116 and the disks 12, 14 therefore will not rotate relative to each other while the suction catheter 154 is in position through a suction catheter pathway 166 created by the axial alignment of the assembly 10. In this manner, a safety lock is created so that a portion of the suction catheter 154 cannot be inadvertently guillotined by a user.

When the suction catheter 154 is withdrawn by a user and returned completely to its sleeve 153, the button 94 of the actuator or button assembly 91 may be depressed to a movement-enabling position (FIGS. 10A-B) while a heath care provider or user also grasps a portion of the distal disk 12 and holds it stationary in order to rotate the proximal disk 14. The rib 44 of the distal disk 12 cooperates with the stop tab 81 on the proximal disk 14 to limit its rotation to, but not by way of limitation, about 180 degrees or less. When the button 94 is depressed completely against the outer edge 30, 70 of the disks 12, 14, the locking tab 116 is moved out of its position through the first notch 31 in the lip 28 of the distal disk 12. In addition, when the button 94 is depressed completely, the blocking portion or plunger 94 is positioned in the first port 20 thereby blocking the first port 20 while the button 94 is held in the depressed position and during the rotation of the disks 12, 14 between the first, second and third positions. At this point in the method, the movement permitting portion 118 of the perimeter edge 113 moves below the lip 28 of the distal disk 12 and the locking tab 116 is positioned further inward, against an inner periphery 43 of the lip 28, thereby releasing the distal and proximal disks 12, 14 from their locked-together position. Rotational movement of the disks 12, 14 is permitted in this movement enabling position of the assembly 10, and rotational movement of at least the proximal disk 14 in a first direction 172 is desirable. The disks 12, 14 remain rotational so long as the movement permitting portion 118 of the perimeter edge 113 of the button 94 does not encounter the second notch 32 on the lip 28 of the distal disk 12. However, when the second notch 32 of the lip 28 crosses the movement permitting portion 118, the second notch 32 permits movement of the perimeter edge 113 outward and the locking tab 116 moves outward through the second notch 32 and against the lip 28 of the distal disk 12 to block further rotation of the distal disk 12. At the same time, the plunger 92 moves outward, out of the first port 20 and into the button housing 90. Therefore, the disks 12 and 14 are locked and port 16 of the distal disk 12 is also locked into a closed position which is non-axially aligned relative to the first and second ports 20, 22, which are also closed and locked. Thus, the port 16 is positioned against a closed distal surface 65 of the proximal disk 14 and the first and second ports 20, 22 are positioned adjacent a closed proximal surface 40 and the seal 48 on the distal disk 12, as shown in FIG. 12. It will be understood that closure caps (illustrated in FIGS. 16-18) may be used to cap the first and second cuffs 24, 26. The assembly 10 desirably remains in the closed position until the button 94 is again depressed.

When the button 94 of the actuator or button assembly 91 is again depressed inward (in the movement-enabling position), and the proximal disk 14 is desirably rotated relative to the distal disk 12 as previously described herein in the first direction 172, the locking tab 116 is again moved out of its position through the second notch 32 of the lip 28 of the distal disk 12. The movement permitting portion 118 of the perimeter edge 113 moves below the lip 28 of the distal disk 12, and the locking tab 116 is positioned again against the inner periphery 43 of the lip 28, thereby holding the button 94 in a depressed position during rotational movement of the disk 12 in the first direction 172. Simultaneously, the plunger 92 is moved into the opening through the first port 20 and first cuff 24 to block the first port 20. The proximal disk 14 desirably continues to rotate relative to the distal disk 12 so long as the lip 28 of the distal disk 12 is moved over the movement permitting portion 118 of the perimeter edge 113 of the button assembly 91. However, when the third notch 33 of the lip 28 crosses the movement permitting portion 118, the third notch 33 permits movement of the perimeter edge 113 and the locking tab 116 moves outward through the third notch 32 and against the lip 28 of the distal disk 12 to block further rotation of the disks 12, 14. In this position, the button 94 moves away from the outer edges 30, 70 of the disks 12, 14. The locking tab 116 of the button assembly 91 is desirably positioned through the third notch 33 of the distal disk 12, thereby holding the disks 12, 14 together in the fixed position. In this position, the plunger 92 is again positioned away from the first port 20 and in the housing 90. Therefore, the port 16 and its cuff 18 are positioned in an axial alignment with the second port 22 and the second cuff 26, as shown in FIG. 13. The alignment creates an opening so that the second port 22 may be connected to a bronchoscope, a bronchial alveolar lavage, and so forth, which will be in communication with the artificial airway 164 and the respiratory tract of a patient, so that a treatments, lavage, observation, and so forth, into the artificial airway and respiratory tract of a patient may be conducted. The first port 20 is positioned in a closed position at this time.

It will be understood that the process may be reversed, and the proximal disk 14 may be moved in a second direction 174 as well as the first direction 172. Further, it will be appreciated that when the button assembly 91 is moved outward, away from the disks 12, 14, the plunger 94 is moved out of a blocking position with respect to the first port 20 and the first cuff 24. In addition, it will also be understood that, should a user not desire to "stop" at one of the first, second or third positions, the user only needs to depress the button 94 and maintain the button 94 in the depressed position until the distal disk 12 is moved into the predetermined first, second or third positions. Finally, it will be appreciated that while the removable suction catheter assembly 150 desirably is releaseably coupled to the first cuff 24 of the first port 20, the suction catheter assembly 150 may also just as easily be coupled to the second cuff 26 of the second port 22 to achieve the same results.

Movement of one disk is relative to the other, because movement of both is allowed, unless a user holds one disk in a stationary position while rotating the other disk. It will be understood that either disk 12, 14 may be held in such a stationary position while the opposite disk is rotated in a rotating position.

The disks 12, 14, the collar 130, and the button assembly 91 are desirably formed from one or more polymers. Examples of these materials include, but are not limited to, polycarbonate, acrylic, and so forth. In addition, the elastomeric seal 48 and O-ring are also desirably formed from one or more polymers. An example of such polymers include, but not by way of limitation, thermoplastic elastomers, and so forth.

In the present embodiment, as illustrated generally in FIGS. 1-15, the cuffs and ports of each disk 12, 14 are positioned at an angle which is not a 90 degree or perpendicular angle relative to the surfaces of the disks 12, 14. The cuffs and ports are provided at the angle(s) shown and/or described herein in order to make the assembly 10 smaller and less "mechanical-looking" to the non-health care observer or patient. That is, angled cuffs and ports permit the assembly to be constructed about 30% smaller than when the cuffs and ports are positioned at a generally perpendicular angle relative to the surfaces of the disks. Moreover, the angled cuffs and ports permit the assembly to be constructed about 40% smaller than when the cuffs and ports are positioned at a generally perpendicular angle relative to the surfaces of the disks. In addition, the smaller footprint of the assembly 10 still importantly permits an axial alignment with the artificial airway 164. In this manner, the assembly 10 carefully controls the access and use of the suction catheter 154 into the artificial airway 164 while remaining a small and barely noticeable component, thereby reducing the anxiety level of a patient who is already coupled to a ventilator and other obtrusive monitoring devices, as well as the anxiety level of his/her family.

Figure 17:
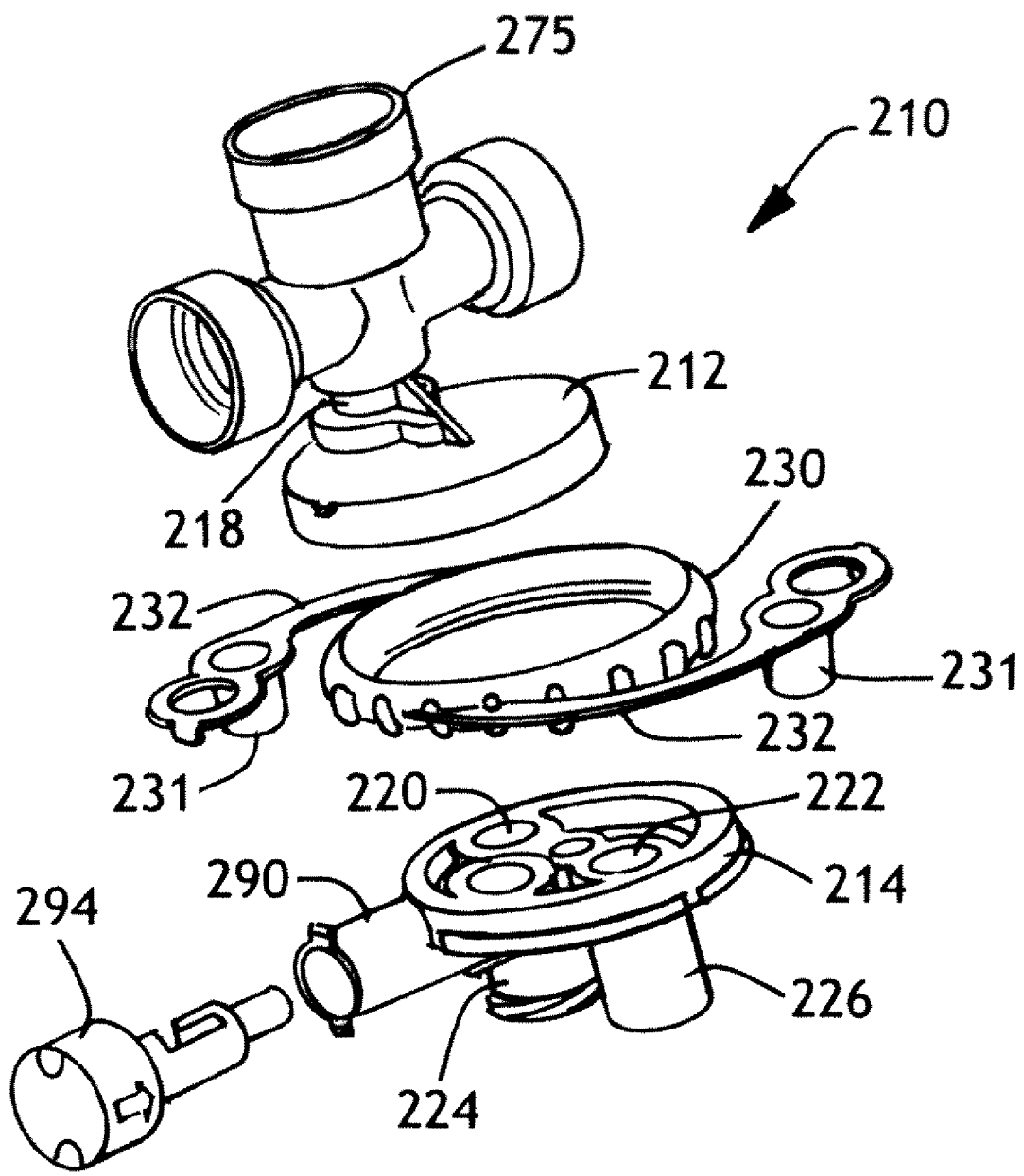
FIG. 17 is an exploded upper perspective view of the respiratory access assembly of FIG. 16.
Figure 18:
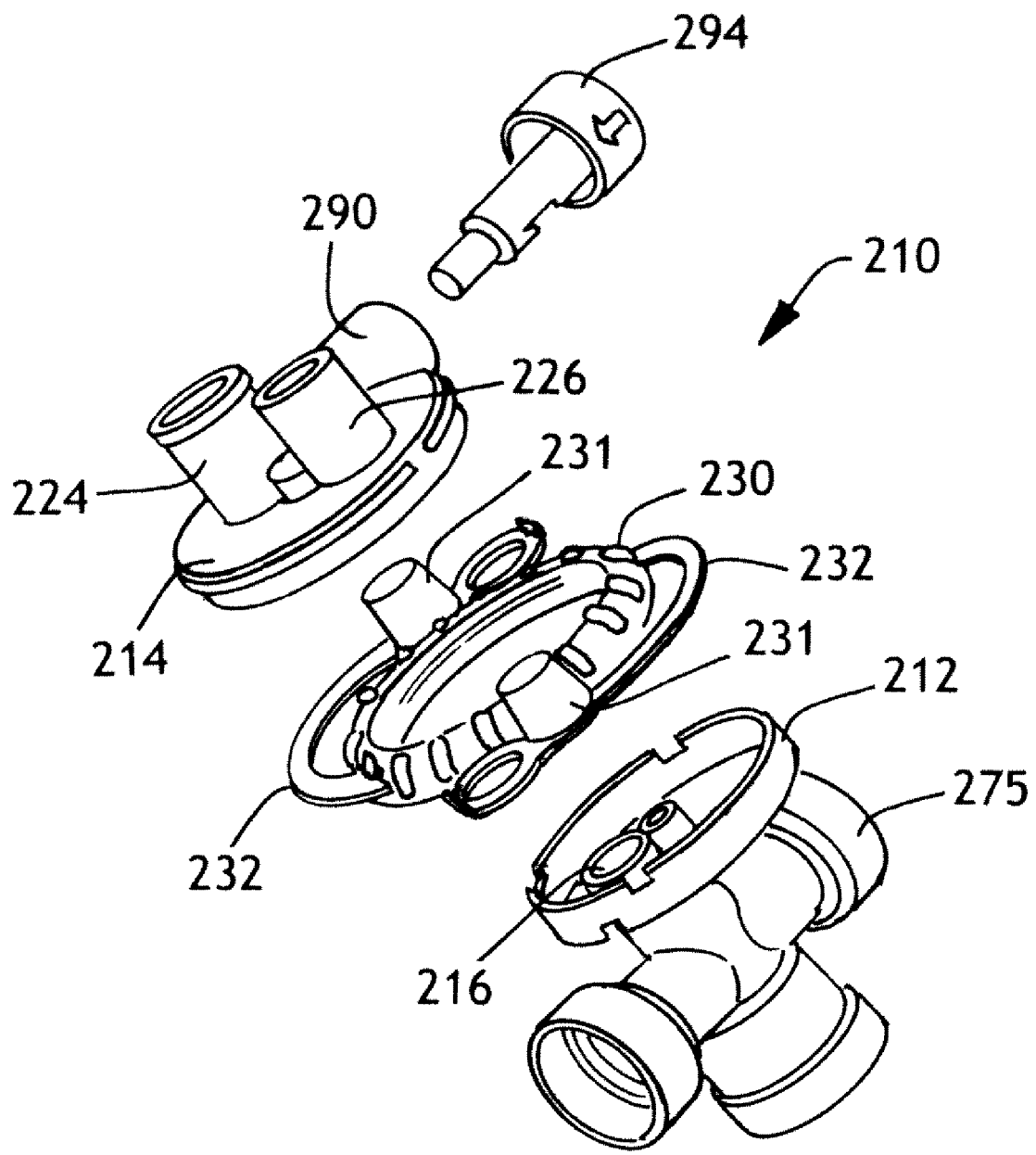
FIG. 18 is an exploded lower perspective view of the respiratory access assembly of FIGS. 16 and 17.
Figure 19:
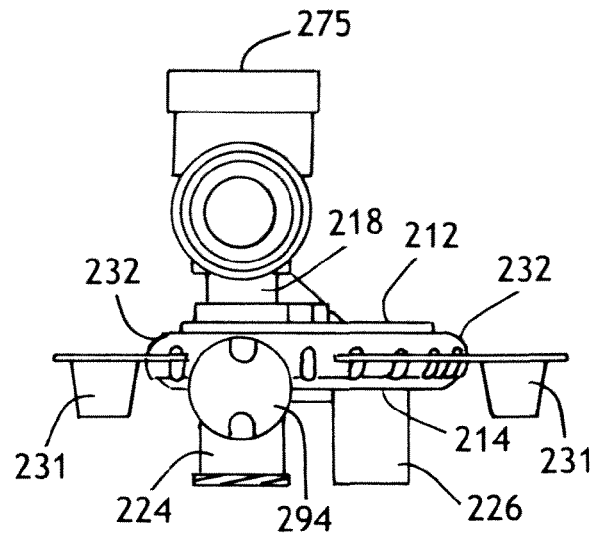
FIG. 19 is a side view of the respiratory access assembly of FIGS. 16-18, showing the port of the distal disk in an axial alignment with the first port of the proximal disk in an open position (first open position)
Figure 20:
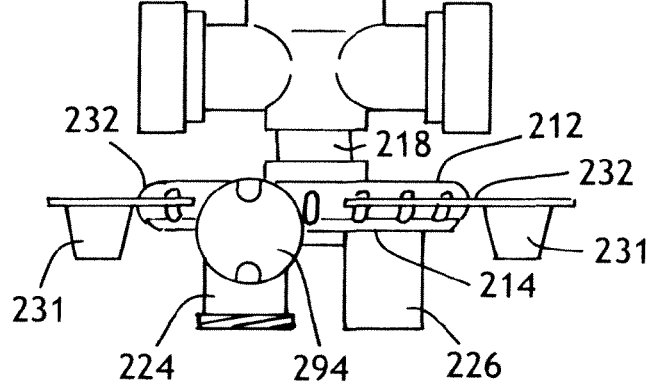
FIG. 20 is a side view of the respiratory access assembly of FIGS. 16-18, showing the port of the distal disk positioned between the first port and the second port of the proximal disk in a closed position (all ports closed)
Figure 21:
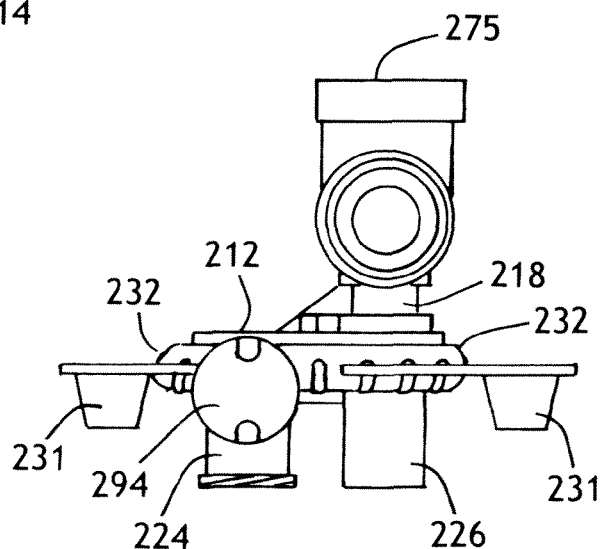
FIG. 21 is a side view of the respiratory access assembly of FIGS. 16-18, showing the port of the distal disk positioned in an axial alignment with the second port of the proximal disk in an open position (second open position)

In another embodiment of the invention, as illustrated in FIGS. 16-21, the assembly 210 is substantially similar to the assembly 10 shown in FIGS. 1-15 and described in detail, except that the port 216 and cuff 218 are provided at about a 90 degree, perpendicular angle relative to the distal plate or disk 212, as shown in FIGS. 19-21. The first and second ports 220, 222 and respective first and second cuffs 224, 226 are also positioned at about a 90 degree, perpendicular angle relative to the proximal plate or disk 214.

Figure 16:
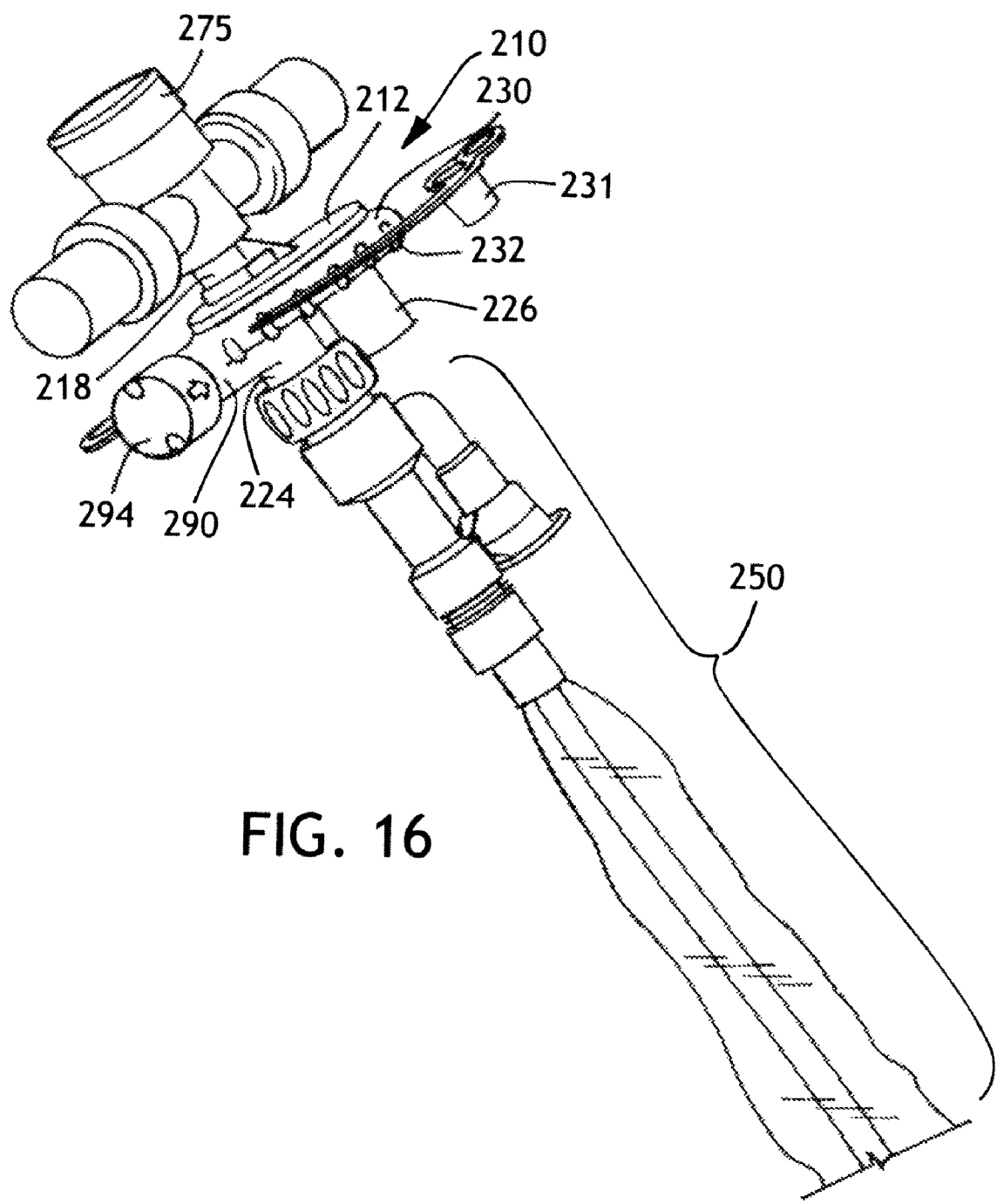
FIG. 16 is a perspective view of another the respiratory access assembly, illustrating the assembly in use and coupled to a respiratory manifold which is attached to an endotracheal tube at a distal end of the assembly, a suction catheter assembly coupled to a proximal end of the assembly.

The actuator or button 294 is shaped differently than the button 94, but operates in the same manner as previously described, and is desirably, but not by way of limitation, biased by a spring (not shown), as illustrated in FIGS. 16-18. Similarly, the button housing 290 has a slightly different shape than the button housing 90, but also operates in the same manner as previously disclosed herein. The collar 230 is slightly different than the collar 130, and it has a pair of caps 231, each of which is attached to the collar 230 by a tether 232.

A pin assembly (not shown) may be used to hold the disks 212, 214, together. Alternatively, the disks 212, 214 may be held together as shown and/or described previously. Desirably, the distal and proximal plates or disks 212, 214 have the same features as previously shown and/or described. In addition, the plates or disks 212, 214 desirably operate in the same manner, with the primary difference being the angle of the ports 216, 220, 222 and their respective cuffs 218, 224, 226. A seal, similar to the seal 48 may be used with the disks 212, 214, or, alternatively, one or more O-rings (not shown) may be used to provide a seal.

The suction catheter assembly 250, illustrated best in FIG. 16, is similar, but not identical, to the suction catheter assembly 150 shown and described previously. The connector or manifold 275 is similar to the connector or manifold 175 previously shown and described herein, except that the connector or manifold 275 includes an additional port which permits an additional connection to the connector or manifold 275.

The assembly 210 desirably has a substantially similar method of operation as that previously illustrated and/or described in detail above for the assembly 10. That is, the assembly 210 is movable between ports and has predetermined positions, i.e., two open positions and one closed position, as previously described herein, and as shown in FIGS. 19-21.

It will be appreciated that the construction of the assembly 210 requires a larger "footprint" or assembly 210 as compared to assembly 10. This is due, in part, to the standard connectors used to connect to cuffs 218, 224 and 226 of ports 216, 222 and 224, respectively, which require sufficient space between at least cuffs 224, 226 in order to connect or couple adequately.

In still another embodiment of the invention, as illustrated in FIGS. 22-27, the assembly 310 is similar to the assemblies 10 and 210 shown in FIGS. 1-15 and FIGS. 16-21, and described previously herein in detail. The distal disk or plate 312 and the proximal disk or plate 314 are provided as rectangular plates which move or slide relative to each other, and against at least a portion of each other. In addition, the ports 316, 320 and 322 and their respective cuffs 318, 324 and 326 are provided at about a 90 degree, perpendicular angle relative to the distal and proximal disks or plates 312, 314, as illustrated in FIGS. 25-27.

Figure 22:
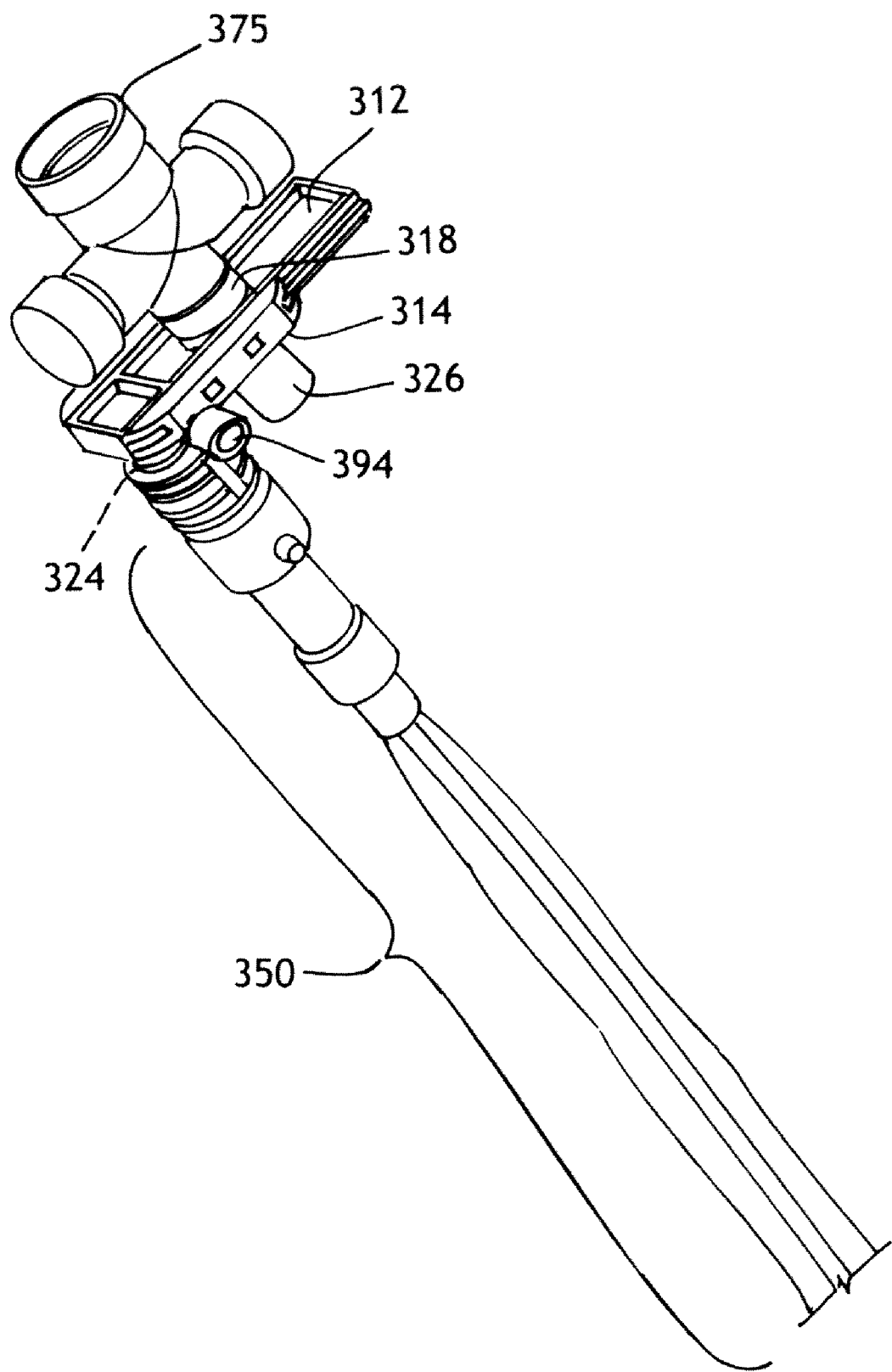
FIG. 22 is a perspective view of yet another the respiratory access assembly, illustrating the assembly in use and coupled to a respiratory manifold which is attached to an endotracheal tube at a distal end of the assembly, a suction catheter assembly coupled to a proximal end of the assembly.
Figure 23:
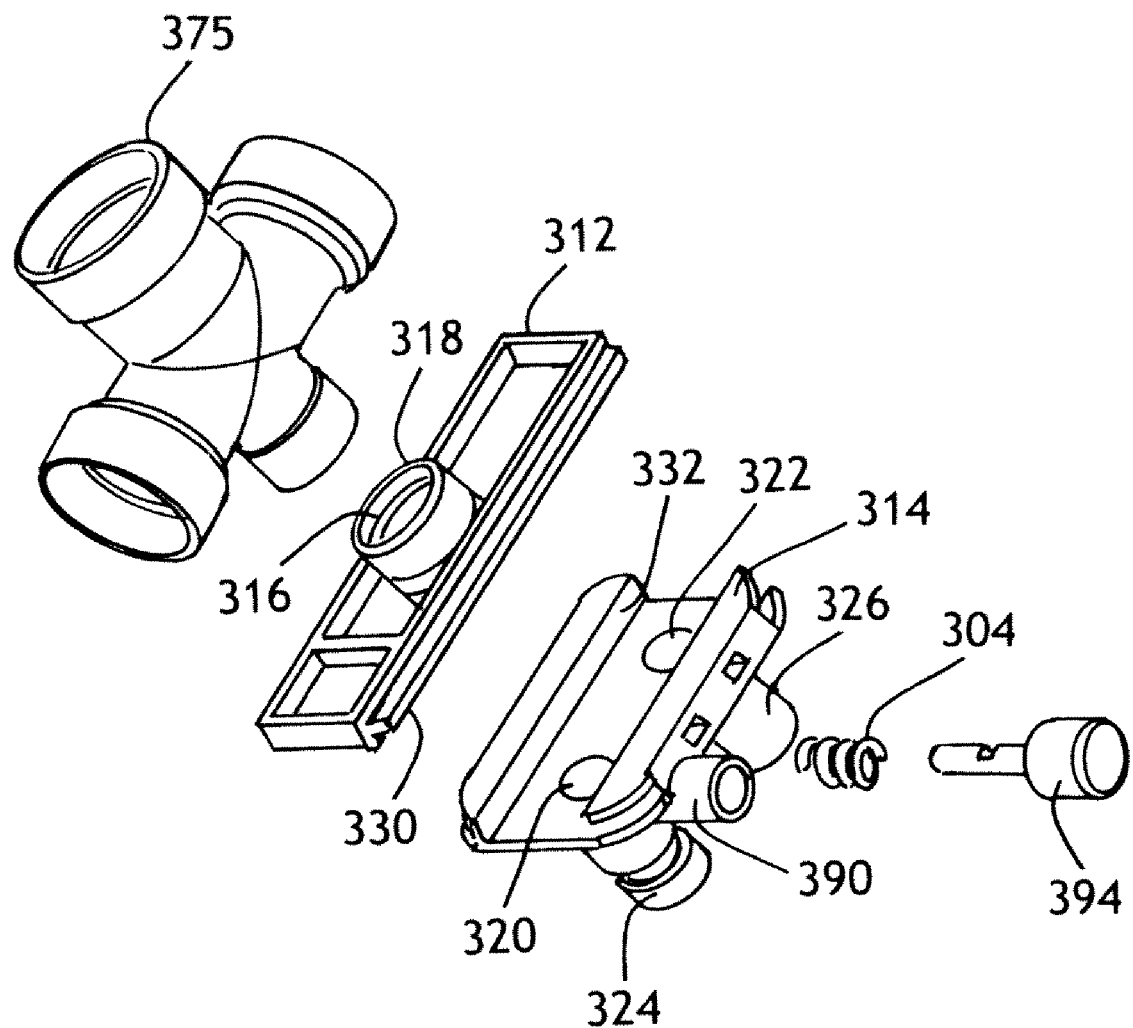
FIG. 23 is an exploded upper perspective view of the respiratory access assembly of FIG. 22.
Figure 24:
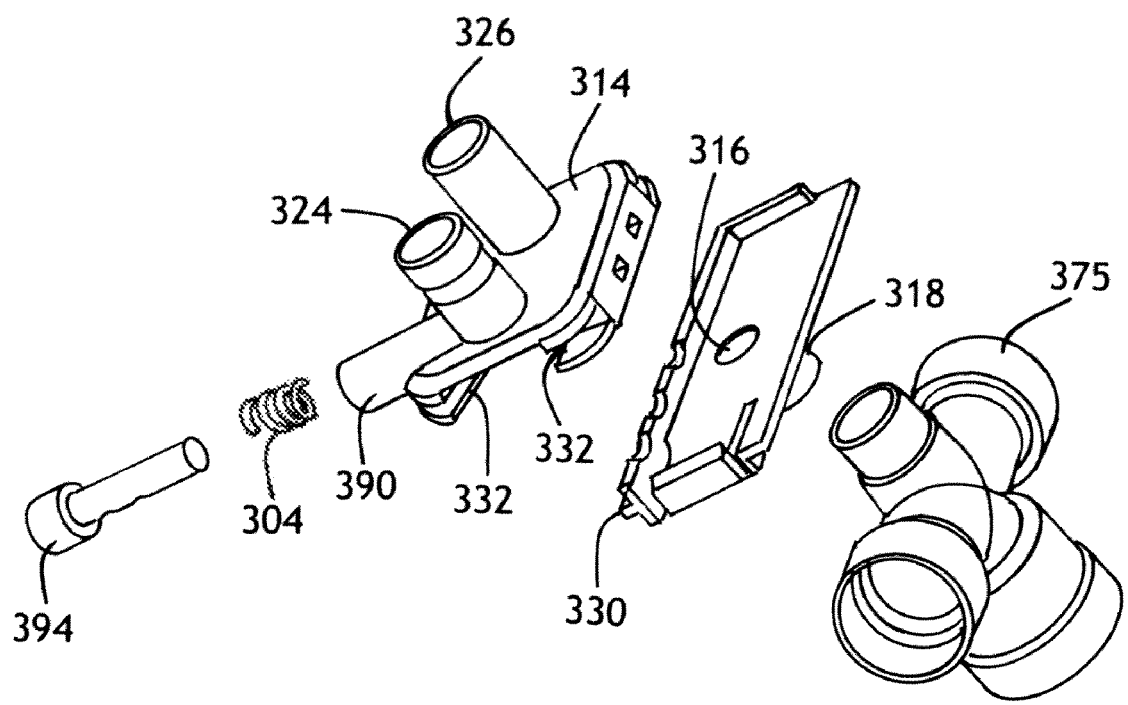
FIG. 24 is an exploded lower perspective view of the respiratory access assembly of FIGS. 22 and 23.

The actuator or button 394 is shaped similarly to button or actuator 294, but desirably operates in the same manner as previously described for button 94, and it may also be biased by a spring 304, as shown in FIGS. 22-24. Similarly, the button housing 390 may have a configuration similar to that of housing 290, but somewhat different than the shape of the button housing 90. The housings 90, 290 and 390 each desirably operates in the same manner as previously shown and/or described herein.

The assembly 310 may include a collar (such as collar 130 or 230) or a pair of collars (not shown) in which one collar extends along each elongated edge 341, or, as illustrated best in FIGS. 22-24, the assembly 310 may be provided without a collar. Caps, with or without tethers, may be provided as part of a collar, or with any component of the assembly 310 (not shown).

In the present embodiment, the distal and proximal disks 312, 314 may have at least one rail 330 which movably position in at least one groove 332, and so forth with a flange or other component (not shown) which permits them to movably couple together, as shown in FIGS. 23 and 24. In another alternative, the disks or plates 312, 314 may be held in a cover which substantially surrounds the disks or plates 312, 314 and which permits them to move or slide relative to each other within the cover (not shown). Desirably, the disks or plates 312, 314 have the same features as previously shown and/or described which permit the disks or plates to move and to be locked into a position. In addition, the disks 312, 314 desirably operate in the same manner as disks 12, 14 and 212, 214, with two primary differences. The first difference is the perpendicular angle of the ports 316, 320, 322 and their related cuffs 318, 324, 326, as illustrated in FIGS. 25-27. The second difference is the straight, rather than rotating movement of the plates 312, 314. The ribs, grooves, and other features provided on the distal plate or disk 12 and the proximal plate or disk 14 are desirably provided in the distal and proximal plates 312, 314, except that the features are provided in a straight, linear alignment rather than a circular alignment, as illustrated generally in FIGS. 23 and 24. One or more seals may be used with the disks 312, 314, or, alternatively, one or more O-rings (not shown) may be used to provide a seal, or a combination of seals and O-rings may be utilized.

The suction catheter assembly 350 is similar, but not identical, to the suction catheter assemblies 250 and 150 shown and described previously. The connector or manifold 375 is substantially similar to the connector or manifold 275 shown in FIGS. 1 and 16 and described previously herein.

The assembly 310 desirably is used and operates in substantially the same manner as previously illustrated and/or described in detail above for the assembly 10 and the assembly 210, except that the plates slide along an longitudinal path rather than rotate. That is, the assembly 310 is desirably movable or slidable between ports and has at least two open positions and may also have one closed position, as previously described herein, and as shown in FIGS. 25-27.

It will be appreciated that the construction of the assembly 310 requires a larger "footprint" than either assembly 210 or assembly 10. This is due, in part, to the space required to permit disks or plates 312, 314 to move or slide relative to each other. In addition, this is also due, in part, to the size of standard connectors used to connect to cuffs 318, 324 and 326 of ports 316, 322 and 324, respectively, which require sufficient space between at least cuffs 324, 326 in order to connect or couple adequately.

In addition, certain components herein have been described and shown at certain angles. However, it will be understood that any component may be positioned at any angle or combination of angles, so long as the assembly operates as shown and/or described herein.

It will be understood that curved or arched plates may be used for the flat or planar disks or planar plates, as well as convex or concave disks or plates. The disks or plates may comprise any configuration, so long as they operate as shown and/or described herein. Similarly, the disks may rotate, pivot, slide, and move in any manner, and so forth, relative to each other, so long as they operate to achieve the result(s) as shown and/or described herein.

The assembly 10, 210, 310 may include more than one port and cuff on the distal disk or plate, and more than two ports and cuffs on the proximal disk or plate. In addition, the assembly 10, 210, 310 may include the connector or manifold 175, 275, 375, or any other manifold known in the art. Further the assembly 10, 210, 310 may include a suction catheter assembly 150, 250, 350, or any other suction catheter assembly known in the art. In a further alternative, the assembly 10, 210, 310 may include a connector or manifold as well as a suction catheter assembly.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A respiratory access assembly, comprising:
   a distal plate having one port, the port adapted to be positioned in operable communication with an artificial airway of a patient;
   a proximal plate including a first port and a second port, the distal plate positioned against the proximal plate in a stacked configuration, each plate configured to move; and
   an actuator positioned adjacent to at least one plate, the actuator cooperating with at least one plate to permit movement of at least one plate when the actuator is positioned in a movement-enabling position, the actuator cooperating with both plates to lock the plates in a fixed position when the actuator is positioned in a locked position, such that the plates are locked into a predetermined position relative to each other, the actuator including a blocking portion which is configured to extend into at least one port when the actuator is positioned in the movement-enabling position, and to withdraw from the one port when the actuator is positioned in the locked position.

2. The respiratory access assembly of claim 1, wherein when the actuator is positioned in the movement-enabling position, at least one plate is movable, and when the port of the distal plate and the first port of the proximal plate are moved into an alignment, the actuator is positioned into the locked position such that the port of the distal plate and the first port of the proximal plate are axially aligned in a first open position, so that an object is movable through the aligned ports.

3. The respiratory access assembly of claim 2, wherein the second port of the proximal plate is positioned in a closed position.

4. The respiratory access assembly of claim 2, wherein the object is a suction catheter.

5. The respiratory access assembly of claim 2, wherein the predetermined position further comprises at least a second open position when the actuator is positioned in the movement-enabling position, at least one plate is movable, and when the port of the distal plate is moved into an alignment with the second port of the proximal plate, the actuator is positioned into a locked position, such that the port of the distal plate and the second port of the proximal plate are axially aligned in a second open position, so that an object is movable through the ports.

6. The respiratory access assembly of claim 5, wherein the first port of the proximal plate is positioned in a closed position.

7. The respiratory access assembly of claim 5, wherein the predetermined position further comprises a closed position of all ports, when the actuator is positioned in a movement-enabling position, at least one plate is movable, and when the port of the distal plate is moved into a position between the first port and the second port and out of alignment with both ports, the actuator is positioned in a locked position, such that the port of the distal plate, the first port and the second port of the proximal plate are in a non-aligned closed position, such that no object is moveable through any of the ports.

8. A respiratory access assembly, comprising:
   a distal plate having one port, the port adapted to be positioned in operable communication with an artificial airway of a patient;
   a proximal plate including a first port and a second port, the distal plate positioned against the proximal plate in a stacked configuration, each plate configured to move relative to each other; and
   a means for enabling movement of the plates and for locking the plates together, such that the plates are movable into a plurality of predetermined positions and are releasably locked in each predetermined position;
   wherein when the means are positioned in a movement-enabling position, the plates are movable, and when the port of the distal plate and the first port of the proximal plate are moved into an alignment, the means are positioned into a locked predetermined position such that the port of the distal plate and the first port of the proximal plate are axially aligned in a first open position, so that an object is movable through the ports and the second port of the proximal plate is positioned in a closed position, and;
   wherein the means comprises an actuator positioned adjacent to both distal and proximal plates, the actuator cooperating with the plates to permit movement thereof when the actuator is positioned in a movement-enabling position, the actuator cooperating with the plates to lock the plates in a fixed position relative to each other when the actuator is positioned a locked position, such that the plates are locked into one of the plurality of predetermined positions, the actuator including a blocking portion which is configured to extend into at least one port when the actuator is positioned in the movement-enabling position, and to withdraw from the one port when the actuator is positioned in the locked position.

9. The respiratory access assembly of claim 8, wherein the plurality of predetermined positions further comprise at least a second open position when the actuator is positioned in the movement-enabling position, such that the plates are movable relative to each other, and when the port of the distal plate and the second part of the proximal plate are moved into an alignment, the actuator is positioned into a locked position such that the port of the distal plate and the second port of the proximal plate are axially aligned in a second open position, so that an object is movable through the ports, and wherein the first port of the proximal plate is positioned in a closed position adjacent the distal plate.

10. The respiratory access assembly of claim 9, wherein the plurality of predetermined positions further comprises a closed position of all ports, such that when the actuator is positioned in a movement-enabling position, the plates are movable relative to each other, and when the port of the distal plate is moved into a position between the first port and the second port and out of alignment with both ports, the actuator is positioned in a locked position, such that the port of the distal plate, the first port and the second port of the proximal plate are in a non-aligned closed position, such that no object is moveable through any of the ports.

11. A method of using a respiratory access assembly, the method comprising:
   providing a respiratory access assembly, including
   a distal plate having one port, the port adapted to be positioned in operable communication with an artificial airway of a patient;
   a proximal plate including a first port and a second port, the first port having a first cuff and the second port having a second cuff, the distal plate positioned against the proximal plate in a stacked configuration, the distal plate and the proximal plate configured to move relative to each other;
   a closed suction catheter assembly comprising at least a connecting end having an opening provided therein, a suction catheter, and a sleeve positioned over the suction catheter and connected to at least the connecting end, wherein the connecting end is releaseably coupled to the first cuff of the first port; and an actuator positioned adjacent to at least one plate and cooperating with the plate to enable at least movement thereof when the actuator is positioned in a movement-enabling position, the actuator cooperating with the plates to lock the plates in a fixed position when the actuator is positioned a locked position, such that the plates are locked together in a predetermined position, the actuator including a blocking portion which is configured to extend into at least one port when the actuator is positioned in the movement-enabling position, and to withdraw from the one port when the actuator is positioned in the locked position;

moving the actuator into a movement-enabling position so that the plates are each movable and simultaneously moving the blocking portion into at least the portion of a port;

moving at least one plate such that the port of the distal plate and the first port of the proximal plate are in an axial alignment in a first open position, the second port simultaneously moved into a closed position adjacent the distal plate;

moving the actuator into a locked position so that the distal plate and the proximal plate are in a locked position and simultaneously moving the blocking portion out of the port, thereby opening the port; and moving the suction catheter through the opened assembly in order to suction secretions from a patient.

12. The method of claim 11, further comprising the step of moving the plates to a predetermined position comprising a second open position which includes moving the actuator into a movement-enabling position so that the plates are movable and simultaneously moving the blocking portion into at least a portion of a port;

moving at least one plate such that the port of the distal plate and the second port of the proximal plate are axially aligned in a second open position, the angled first port simultaneously moved into a closed position adjacent the distal plate; and moving the actuator into a locked position so that the distal plate and the proximal plate are in a locked position and simultaneously moving the blocking portion out of the port, thereby allowing at least an object to move through both axially aligned ports.

13. The method of claim 12, further comprising the step of moving the plate to a predetermined position comprising a closed position of all ports which includes moving the actuator into a movement-enabling position so that the plates are movable and simultaneously moving the blocking portion into at least a portion of a port;

moving the movable plate such that the port of the distal plate is positioned between the first port and the second port of the proximal plate and out of an alignment with both ports so that all ports are positioned in a non-aligned closed position, the port of the distal plate positioned in a closed position adjacent a portion of the proximal plate and the first port and the second port of the proximal plate positioned in a closed position adjacent a portion of the distal plate such that no object is moveable through any of the ports.

* * * * *